(12) United States Patent
Wagner et al.

(10) Patent No.: US 7,047,071 B2
(45) Date of Patent: May 16, 2006

(54) PATIENT STRATIFICATION FOR IMPLANTABLE SUBCUTANEOUS CARDIAC MONITORING AND THERAPY

(75) Inventors: Darrell Orvin Wagner, Isanti, MN (US); Adam W. Cates, Minneapolis, MN (US); Curtis Charles Lindstrom, Roseville, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 215 days.

(21) Appl. No.: 10/799,341

(22) Filed: Mar. 12, 2004

(65) Prior Publication Data
US 2004/0220641 A1    Nov. 4, 2004

Related U.S. Application Data

(60) Provisional application No. 60/462,272, filed on Apr. 11, 2003.

(51) Int. Cl.
*A61N 1/18* (2006.01)
*A61N 1/38* (2006.01)

(52) U.S. Cl. .................... 607/4; 607/5; 607/10; 607/28

(58) Field of Classification Search ............ 607/27–28, 607/4–5, 9–10, 145, 149–150
See application file for complete search history.

(56) References Cited

U.S. PATENT DOCUMENTS

| | | |
|---|---|---|
| 4,562,841 A | 1/1986 | Brockway et al. |
| 4,953,551 A | 9/1990 | Mehra et al. |
| 5,036,849 A | 8/1991 | Hauck et al. |
| 5,133,353 A | 7/1992 | Hauser |
| 5,170,784 A | 12/1992 | Ramon et al. |
| 5,179,945 A | 1/1993 | Van Hofwegen et al. |
| 5,203,348 A | 4/1993 | Dahl et al. |
| 5,209,229 A | 5/1993 | Gilli |
| 5,230,337 A | 7/1993 | Dahl et al. |

(Continued)

FOREIGN PATENT DOCUMENTS

WO    WO 92/20402    11/1992

OTHER PUBLICATIONS

Gould L, Reddy CV, Brevetti GC, Cifarelli F, Maghazeh P, Shin CS. His bundle electrograms in 51 patients requiring permanent transvenous pacemakers. J Thorac Cardiovasc Surg. Jul. 1977;74(1):28-36.*

Renee Hartz et al., *New Approach to Defibrillator Insertion*, J. Thoracic Cardiovascular Surgery, vol. 97, pp. 920-922 (1989).

(Continued)

*Primary Examiner*—Carl Layno
*Assistant Examiner*—Shevon Johnson
(74) *Attorney, Agent, or Firm*—Hollingsworth & Funk, LLC

(57) ABSTRACT

Systems and methods of verifying that implantable cardiac devices operate as intended in a particular patient involve one or more of determining proper placement of system components, determining stimulus levels useful for individual patient stratification, and determining stimulus levels that indicate efficacy of devices, implantable within a given patient. A pacing stimulus set at a surface pacing level is delivered to a patient's heart using surface electrodes. The patient is determined to not be a candidate for implantation of a subcutaneous defibrillation system if the surface pacing level needed to capture the heart exceeds a predetermined level. The patient may be determined to be a candidate for implantation of a subcutaneous system if the surface pacing level needed to effect capture is within an acceptance level. Such determinations are preferably based on a proportionality relationship between a subcutaneous defibrillation level and a surface pacing level.

57 Claims, 14 Drawing Sheets

U.S. PATENT DOCUMENTS

| | | |
|---|---|---|
| 5,261,400 A | 11/1993 | Bardy |
| 5,284,136 A | 2/1994 | Hauck et al. |
| 5,292,338 A | 3/1994 | Bardy |
| 5,300,106 A | 4/1994 | Dahl et al. |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,318,597 A | 6/1994 | Hauck et al. |
| 5,331,966 A | 7/1994 | Bennett et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,439,482 A | 8/1995 | Adams et al. |
| 5,441,518 A | 8/1995 | Adams et al. |
| 5,468,254 A | 11/1995 | Hahn et al. |
| 5,531,779 A | 7/1996 | Dahl et al. |
| 5,540,727 A | 7/1996 | Tockman et al. |
| 5,545,186 A | 8/1996 | Olson et al. |
| 5,545,202 A | 8/1996 | Dahl et al. |
| 5,603,732 A | 2/1997 | Dahl et al. |
| 5,620,466 A | 4/1997 | Haefner et al. |
| 5,634,938 A | 6/1997 | Swanson et al. |
| 5,641,326 A | 6/1997 | Adams |
| 5,662,688 A | 9/1997 | Haefner et al. |
| 5,697,953 A | 12/1997 | Kroll et al. |
| 5,704,365 A | 1/1998 | Albrecht et al. |
| 5,716,382 A * | 2/1998 | Snell ........................... 607/30 |
| 5,724,984 A | 3/1998 | Arnold et al. |
| 5,827,326 A | 10/1998 | Kroll et al. |
| 5,836,987 A | 11/1998 | Baumann et al. |
| 5,855,593 A | 1/1999 | Olson et al. |
| 5,895,414 A | 4/1999 | Sanchez-Zambrano |
| 5,916,243 A | 6/1999 | KenKnight et al. |
| 5,957,956 A | 9/1999 | Kroll et al. |
| 6,044,298 A | 3/2000 | Salo et al. |
| 6,055,454 A | 4/2000 | Heemels |
| 6,141,581 A | 10/2000 | Olson et al. |
| 6,148,230 A | 11/2000 | KenKnight |
| 6,259,947 B1 | 7/2001 | Olson et al. |
| 6,280,462 B1 | 8/2001 | Hauser et al. |
| 6,438,410 B1 | 8/2002 | Hsu et al. |
| 6,487,443 B1 | 11/2002 | Olson et al. |
| 6,491,639 B1 | 12/2002 | Turcott |
| 6,512,940 B1 | 1/2003 | Brabec et al. |
| 6,522,915 B1 | 2/2003 | Ceballos et al. |
| 6,564,106 B1 | 5/2003 | Guck et al. |
| 6,567,697 B1 * | 5/2003 | Kroll et al. ..................... 607/5 |
| 6,607,509 B1 | 8/2003 | Bobroff et al. |
| 6,615,083 B1 | 9/2003 | Kupper |
| 6,622,046 B1 | 9/2003 | Fraley et al. |
| 6,628,986 B1 | 9/2003 | Mouchawar et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1 | 6/2002 | Heinrich et al. |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2003/0004546 A1 | 1/2003 | Casey |
| 2003/0004552 A1 | 1/2003 | Plombon et al. |
| 2003/0023175 A1 | 1/2003 | Arzbaecher et al. |
| 2003/0036778 A1 | 2/2003 | Ostroff et al. |
| 2003/0045904 A1 | 3/2003 | Bardy et al. |
| 2003/0069609 A1 | 4/2003 | Thompson |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0212436 A1 | 11/2003 | Brown |

OTHER PUBLICATIONS

Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek Malik, *Defibrillation Threshold (DFT) Model of a Fully Subcutaneous ICD System*, Europace Supplements, vol. 2, Jun. 2001, p. B83, col. 778, best copy available.

Stirbis et al., *Optmizing the Shape of Implanted Artificial Pacemakers*, Kaunas Medical Institute. Translated from Meditsinskaya Tekhnika, No. 6, pp. 25-27 (1986).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

\* cited by examiner

PATIENT STRATIFICATION FOR IMPLANTABLE SUBCUTANEOUS CARDIAC MONITORING AND THERAPY

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to implantable medical devices and, more particularly, to systems and methods for determining patient stratification, and determining efficacy of devices implantable within a given patient.

BACKGROUND OF THE INVENTION

The healthy heart produces regular, synchronized contractions. Rhythmic contractions of the heart are normally controlled by the sinoatrial (SA) node, which are specialized cells located in the upper right atrium. The SA node is the normal pacemaker of the heart, typically initiating 60–100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating the arrythmias described above.

Implantable cardioverter/defibrillators (ICDs) have been used as an effective treatment for patients with serious cardiac arrhythmias. For example, a typical ICD includes one or more endocardial leads to which at least one defibrillation electrode is connected. Such ICDs are capable of delivering high-energy shocks to the heart, interrupting the ventricular tachyarrythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. The primary reasons for this unfortunate reality include the limited number of physicians qualified to perform transvenous lead/electrode implantation, a limited number of surgical facilities adequately equipped to accommodate such cardiac procedures, and a limited number of the at-risk patient population that may safely undergo the required endocardial or epicardial lead/electrode implant procedure.

SUMMARY OF THE INVENTION

The present invention is directed to systems and methods for evaluating whether implantable cardiac monitoring/stimulation devices are appropriate for a particular patient. The present invention is also directed to systems and methods for determining proper placement of components of these implantable systems.

Embodiments of the present invention include those directed to patient screening methods involving delivery of a pacing stimulus to a patient's heart using one or more surface electrodes. The pacing stimulus is delivered at a surface pacing level. If the surface pacing level needed to capture the patient's heart exceeds a predetermined upper level, it is determined that the patient is not a candidate for implantation of a subcutaneous cardiac stimulation system, such as a subcutaneous defibrillation device. The patient may be determined to be a candidate for implantation of the subcutaneous defibrillation device if the surface pacing level needed to capture the patient's heart is at or below an acceptance level. Defibrillation testing of the patient may be performed using a cardiac defibrillation stimulus delivered at a surface defibrillation level if the surface pacing level needed to capture the heart of the patient is above the acceptance level and does not exceed the predetermined upper limit.

A patient screening and/or electrode positioning approach of the present invention exploits a relationship discovered by the inventors involving the surface pacing level and the subcutaneous defibrillation level. Data indicate that the current associated with surface pacing is proportionally related to the energy associated with subcutaneous defibrillation. More particularly, the current required to effect capture of a patient's heart using a surface pacing stimulus corresponds to an energy level required to subcutaneously defibrillate the patient's heart, based on this proportionality relationship. This correspondence between surface pacing current and subcutaneous defibrillation energy may be used for a variety of purposes, including, for example, determining whether or not a given patient is a candidate for a given subcutaneous defibrillation device. For certain patients, this determination may eliminate the need to perform defibrillation testing at implant.

A system implemented in accordance with the present invention includes a pulse generator configured to deliver a pacing stimulus at a pacing level. The system may also include detection circuitry and a number of surface electrodes coupled to the pulse generator and to the detection circuitry. The surface electrodes are configured for positioning on a thorax of a patient relative to the patient's heart. The system further includes a user interface and a controller coupled to the pulse generator, detection circuitry, and surface electrodes. The controller determines suitability of the patient to receive a subcutaneous defibrillation device based at least in part on detection of capture or non-capture resulting from delivery of the pacing stimulus at the pacing level. The controller is configured to operate cooperatively with the user interface to provide a user with an indication of the suitability of the patient to receive the subcutaneous defibrillation device. Some or all of the components of the system may be situated within/on a housing. The housing may include a handle and be configured for hand-held portability.

In another embodiment of the present invention, the electrodes may be affixed to a rigid electrode support assembly, and have a predefined positional relationship relative to one another. A patient screening method using this type of electrode arrangement may involve the steps of providing at least two surface electrodes connected together and having a fixed spatial relationship. The electrodes may then be located on a thorax of a patient, such as having a first electrode near the apex of the patient's heart, and having a second electrode at a left pectoral region of the patient's thorax.

A surface pacing threshold may be determined for effecting cardiac capture using the surface electrodes. The patient may be selected or rejected as a candidate for implantation of a subcutaneous defibrillation system based on the surface pacing threshold. If the current positioning is not acceptable, the rigid electrode support assembly may be rotated about the first electrode, for example, by maintaining the first electrode at the heart's apex, but rotating the second electrode to another location. For example, the second electrode may be rotated from the left pectoral region of the patient's thorax to a right pectoral location of the patient's thorax in search of a more optimum pacing and/or defibrillation threshold. The rigid electrode support assembly maintains the predefined positional relationship of the electrodes as they are positioned and rotated on the patient's thorax.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
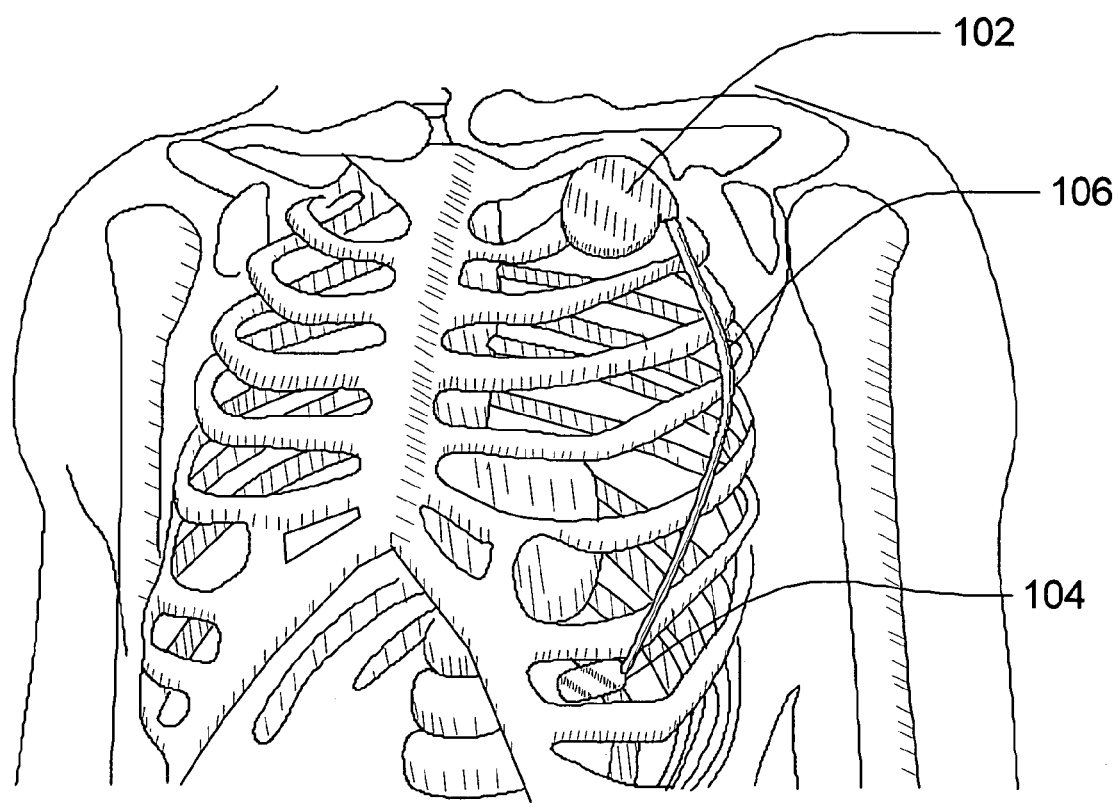
FIGS. 1A and 1B are views of a transthoracic cardiac sensing and/or stimulation device as implanted in a patient in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which is shown by way of illustration, various embodiments in which the invention may be practiced. It is to be understood that other embodiments may be utilized, and structural and functional changes may be made without departing from the scope of the present invention.

System and methods of the present invention may include one or more of the features, structures, methods, or combinations thereof described hereinbelow. For example, patient stratification and/or electrode positioning systems and methods in accordance with the present invention may be implemented to include one or more of the advantageous features and/or processes described below. It is intended that such devices and methods need not include all of the features described herein, but may be implemented to include selected features that provide for unique structures and/or functionality. Such devices and methods may be implemented to provide a variety of therapeutic and/or diagnostic functions.

Embodiments of the present invention are directed to systems and methods for determining if a patient is a candidate for an implantable cardiac monitoring/stimulation device, such as a subcutaneous defibrillation device. Embodiments of the present invention are also directed to systems and methods for determining suitable electrode placement locations to improve the performance of the implantable system. One such implantable device, termed an implantable transthoracic cardiac sensing and/or stimulation (ITCS) device, is described herein to include various advantageous features and/or processes. It is understood that the description of features and processes within the context of an ITCS device is provided for non-limiting illustrative purposes only. For example, various features and processes described herein may be implemented for patient stratification and electrode placement optimization for devices such as cardiac monitors, diagnostic devices, pacemakers, cardioverters/defibrillators, resynchronizers, and the like, including those devices disclosed in the various patents incorporated herein by reference.

In general terms, an ITCS device may be implanted under the skin in the chest region of a patient. The ITCS device may, for example, be implanted subcutaneously such that all or selected elements of the device are located on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively located at different regions near, around, in, or on the heart. Examples of electrode configurations, elements of which may be located in accordance with the present invention, are disclosed in commonly owned U.S. patent application Ser. No. 10/465,520, filed Jun. 19, 2003, which is hereby incorporated herein by reference in its entirety.

In one configuration, the primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature. In another implementation, one or more electrodes may be located in direct contact with the heart, great vessel or coronary vasculature, such as via one or more leads. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, elements of which may be incorporated in an ITCS device of a type contemplated herein, are disclosed in commonly owned U.S. Pat. Nos. 5,133,353; 5,179,945; 5,314,459; 5,318,597; 5,620,466; and 5,662,688, which are hereby incorporated herein by reference in their respective entireties.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, elements of which may be incorporated in an ITCS device of a type contemplated herein, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference in their respective entireties. It is understood that ITCS device configurations may provide for non-physiologic pacing support in addition to, or to the exclusion of, bradycardia and/or anti-tachycardia pacing therapies.

An ITCS device may implement functionality traditionally provided by cardiac diagnostic devices or cardiac monitors as are known in the art, alternatively or additionally to providing cardioversion/defibrillation therapies. Examples of cardiac monitoring circuitry, structures and functionality, elements of which may be incorporated in an ITCS device of a type contemplated herein, are disclosed in commonly owned U.S. Pat. Nos. 5,313,953; 5,388,578; and 5,411,031, which are hereby incorporated herein by reference in their respective entireties.

An ITCS device may implement various anti-tachyarrhythmia therapies, such as tiered therapies. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

An ITCS device may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

Figure 1B:
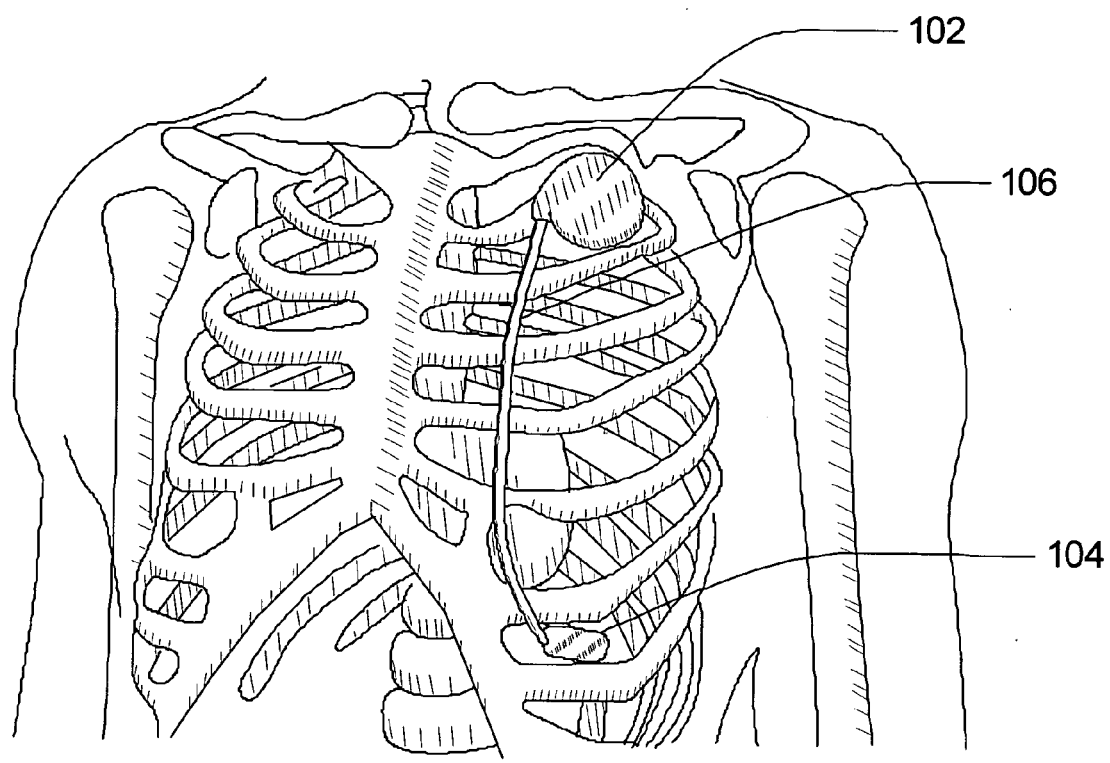

Referring now to FIGS. 1A and 1B of the drawings, there is shown a configuration of an ITCS device implanted in the chest region of a patient at different locations. In the particular configuration shown in FIGS. 1A and 1B, the ITCS device includes a housing 102 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures may be implemented in combination with other components and functionality, and that the depiction of such components and functionality in individual or integral form is for purposes of clarity of explanation, and not of limitation.

Communications circuitry is disposed within the housing 102 for facilitating communication between the ITCS device and an external communication device, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed.

In the configuration shown in FIGS. 1A and 1B, a subcutaneous electrode 104 may be positioned under the skin in the chest region and situated distal from the housing 102. The subcutaneous and, if applicable, housing electrode(s) may be located about the heart at various locations and orientations, such as at various anterior and/or posterior locations relative to the heart. The subcutaneous electrode 104 is electrically coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 1A and 1B).

In accordance with a further configuration, the lead assembly 106 includes a rigid electrode support assembly, such as a rigid elongated structure that positionally stabilizes the subcutaneous electrode 104 with respect to the housing 102. In this configuration, the rigidity of the elongated structure maintains a desired spacing between the subcutaneous electrode 104 and the housing 102, and a desired orientation of the subcutaneous electrode 104/housing 102 relative to the patient's heart. The elongated structure may be formed from a structural plastic, composite or metallic material, and includes, or is covered by, a biocompatible material. Appropriate electrical isolation between the housing 102 and subcutaneous electrode 104 is provided in cases where the elongated structure is formed from an electrically conductive material, such as metal.

In one configuration, the rigid electrode support assembly and the housing 102 define a unitary structure (i.e., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the rigid electrode support assembly and housing 102. The header block arrangement may be provided on the housing 102 or the rigid electrode support assembly. Alternatively, a mechanical/electrical coupler may be used to establish mechanical and electrical connections between the rigid electrode support assembly and housing 102. In such a configuration, a variety of different electrode support assemblies of varying shapes, sizes, and electrode configurations may be made available for physically and electrically connecting to a standard ITCS device housing 102.

An ITCS device may incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference in their respective entireties.

Depending on the configuration of a particular ITCS device, a delivery system can advantageously be used to facilitate proper placement and orientation of the ITCS device housing and subcutaneous electrode(s). According to one configuration of such a delivery system, a long metal rod similar to conventional trocars can be used to perform small diameter blunt tissue dissection of the subdermal layers. This tool may be pre-formed straight or curved to facilitate placement of the subcutaneous electrode, or it may be flexible enough to allow the physician to shape it appropriately for a given patient. Examples of delivery tools, elements of which can be incorporated into an ITCS device delivery tool, are disclosed in commonly owned U.S. Pat. No. 5,300,106; U.S. patent application Ser. No. 10/625,833, filed Jul. 23, 2003; U.S. patent application Ser. No. 10/625,826 filed Jul. 23, 2003; and U.S. patent application Ser. No. 10/653,456 filed Sep. 2, 2003; which are hereby incorporated herein by reference.

Figure 1C:
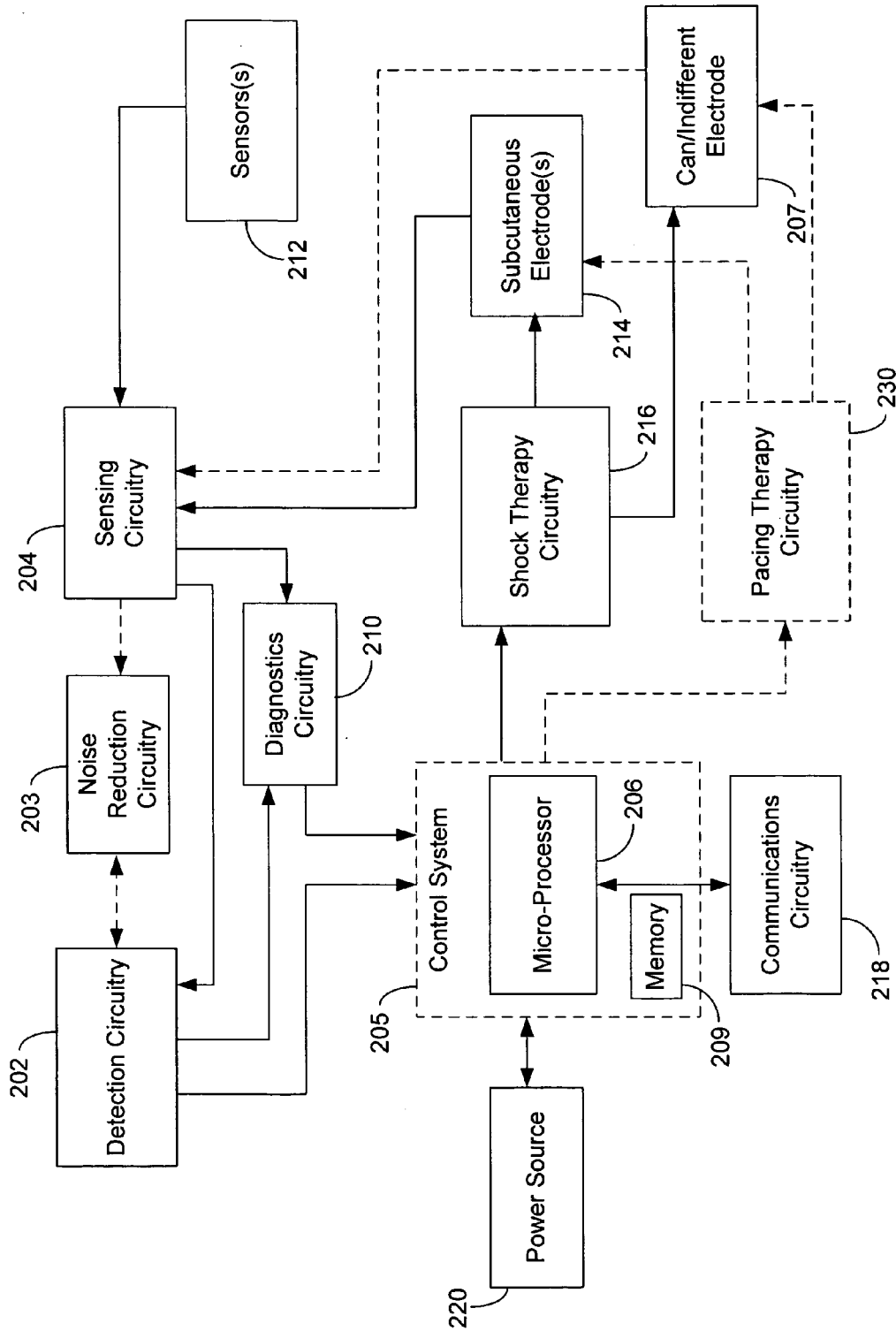
FIG. 1C is a block diagram showing various components of a transthoracic cardiac sensing and/or stimulation device in accordance with an embodiment of the present invention.

FIG. 1C is a block diagram depicting various components of an ITCS device in accordance with one configuration. According to this configuration, the ITCS device incorporates a processor-based control system 205 which includes a micro-processor 206 coupled to appropriate memory (volatile and non-volatile) 209, it being understood that any logic-based control architecture may be used. The control system 205 is coupled to circuitry and components to sense, detect, and analyze electrical signals produced by the heart and deliver electrical stimulation energy to the heart under predetermined conditions to treat cardiac arrhythmias. In certain configurations, the control system 205 and associated components also provide pacing therapy to the heart. The electrical energy delivered by the ITCS device may be in the form of low energy pacing pulses or high-energy pulses for cardioversion or defibrillation.

Cardiac signals are sensed using the subcutaneous electrode(s) 214 and the can or indifferent electrode 207 provided on the ITCS device housing. Cardiac signals may also be sensed using only the subcutaneous electrodes 214, such as in a non-active can configuration. As such, unipolar, bipolar, or combined unipolar/bipolar electrode configurations may be employed. The sensed cardiac signals are received by sensing circuitry 204, which includes sense amplification circuitry and may also include filtering circuitry and an analog-to-digital (A/D) converter. The sensed cardiac signals processed by the sensing circuitry 204 may be received by noise reduction circuitry 203, which may further reduce noise for signals used by the detection circuitry 202. Noise reduction circuitry 203 may also be incorporated after detection circuitry 202 in cases where high power or computationally intensive noise reduction algorithms are required.

In the illustrative configuration shown in FIG. 1C, the detection circuitry 202 is coupled to, or otherwise incorporates, noise reduction circuitry 203. The noise reduction circuitry 203 operates to improve the signal-to-noise ratio of sensed cardiac signals by removing noise content of the sensed cardiac signals introduced from various sources. Typical types of transthoracic cardiac signal noise includes electrical noise and noise produced from skeletal muscles, for example.

Detection circuitry 202 typically includes a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 202 to detect and verify the presence and severity of an arrhythmic episode. Examples of arrhythmia detection and discrimination circuitry, structures, and techniques, elements of which may be implemented by an ITCS device of a type contemplated herein, are disclosed in commonly owned U.S. Pat. Nos. 5,301,677 and 6,438,410, which are hereby incorporated herein by reference in their respective entireties.

The detection circuitry 202 communicates cardiac signal information to the control system 205. Memory circuitry 209 of the control system 205 contains parameters for operating in various sensing, defibrillation, and pacing modes, and stores data indicative of cardiac signals received by the detection circuitry 202. The memory circuitry 209 may also be configured to store historical ECG and therapy data, which may be used for various purposes and transmitted to an external receiving device as needed or desired.

In certain configurations, the ITCS device may include diagnostics circuitry 210. The diagnostics circuitry 210 typically receives input signals from the detection circuitry 202 and the sensing circuitry 204. The diagnostics circuitry 210 provides diagnostics data to the control system 205, it being understood that the control system 205 may incorporate all or part of the diagnostics circuitry 210 or its functionality. The control system 205 may store and use information provided by the diagnostics circuitry 210 for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

According to a configuration that provides cardioversion and defibrillation therapies, the control system 205 processes cardiac signal data received from the detection circuitry 202 and initiates appropriate tachyarrhythmia therapies to terminate cardiac arrhythmic episodes and return the heart to normal sinus rhythm. The control system 205 is coupled to shock therapy circuitry 216. The shock therapy circuitry 216 is coupled to the subcutaneous electrode(s) 214 and the can or indifferent electrode 207 of the ITCS device housing. Upon command, the shock therapy circuitry 216 delivers cardioversion and defibrillation stimulation energy to the heart in accordance with a selected cardioversion or defibrillation therapy. In a less sophisticated configuration, the shock therapy circuitry 216 is controlled to deliver defibrillation therapies, in contrast to a configuration that provides for delivery of both cardioversion and defibrillation therapies. Examples of ICD high energy delivery circuitry, structures and functionality, elements of which may be incorporated in an ITCS device of a type contemplated herein, are disclosed in commonly owned U.S. Pat. Nos. 5,372,606; 5,411,525; 5,468,254; and 5,634,938, which are hereby incorporated herein by reference in their respective entireties.

In accordance with another configuration, an ITCS device may incorporate a cardiac pacing capability in addition to cardioversion and/or defibrillation capabilities. As is shown in dotted lines in FIG. 1C, the ITCS device may include pacing therapy circuitry 230, which is coupled to the control system 205 and the subcutaneous and can/indifferent electrodes 214, 207. Upon command, the pacing therapy circuitry delivers pacing pulses to the heart in accordance with a selected pacing therapy. Control signals, developed in accordance with a pacing regimen by pacemaker circuitry within the control system 205, are initiated and transmitted to the pacing therapy circuitry 230 where pacing pulses are generated. A pacing regimen may be modified by the control system 205.

A number of cardiac pacing therapies are described herein, which are particularly useful in a transthoracic cardiac stimulation device. Such cardiac pacing therapies may be delivered via the pacing therapy circuitry 230 as shown in FIG. 1C. Alternatively, cardiac pacing therapies may be delivered via the shock therapy circuitry 216, which effectively obviates the need for separate pacemaker circuitry.

The ITCS device shown in FIG. 1C may be configured to receive signals from one or more physiologic and/or non-physiologic sensors 212. Depending on the type of sensor employed, signals generated by the sensors 212 may be communicated to transducer circuitry coupled directly to the detection circuitry or indirectly via the sensing circuitry. It is noted that certain sensors 212 may transmit sense data to the control system 205 without processing by the detection circuitry 202.

Communications circuitry 218 is coupled to the microprocessor 206 of the control system 205. The communications circuitry 218 allows the ITCS device to communicate with one or more receiving devices or systems situated external to the ITCS device. By way of example, the ITCS device may communicate with a patient-worn, portable or bedside communication system via the communications circuitry 218. In one configuration, one or more physiologic or non-physiologic sensors (subcutaneous, cutaneous, or external of patient) may be equipped with a short-range wireless communication interface, such as an interface conforming to a known communications standard, such as Bluetooth or IEEE 802 standards. Data acquired by such sensors may be communicated to the ITCS device via the communications circuitry 218. It is noted that physiologic or non-physiologic sensors equipped with wireless transmitters or transceivers may communicate with a receiving system external of the patient.

The communications circuitry 218 may allow the ITCS device to communicate with an external programmer. In one configuration, the communications circuitry 218 and the programmer unit (not shown) use a wire loop antenna and a radio frequency telemetric link, as is known in the art, to receive and transmit signals and data between the programmer unit and communications circuitry 218. In this manner, programming commands and data are transferred between the ITCS device and the programmer unit during and after implant. Using a programmer, a physician is able to set or modify various parameters used by the ITCS device. For example, a physician may set or modify parameters affecting sensing, detection, pacing, and defibrillation functions of the ITCS device, including pacing and cardioversion/defibrillation therapy modes.

Typically, the ITCS device is encased and hermetically sealed in a housing suitable for implanting in a human body as is known in the art. Power to the ITCS device is supplied by an electrochemical power source 220 housed within the ITCS device. In one configuration, the power source 220 includes a rechargeable battery. According to this configuration, charging circuitry is coupled to the power source 220 to facilitate repeated non-invasive charging of the power source 220. The communications circuitry 218, or separate receiver circuitry, is configured to receive RF energy transmitted by an external RF energy transmitter. The ITCS device may, in addition to a rechargeable power source, include a non-rechargeable battery. It is understood that a rechargeable power source need not be used, in which case a long-life non-rechargeable battery is employed.

Figure 1D:
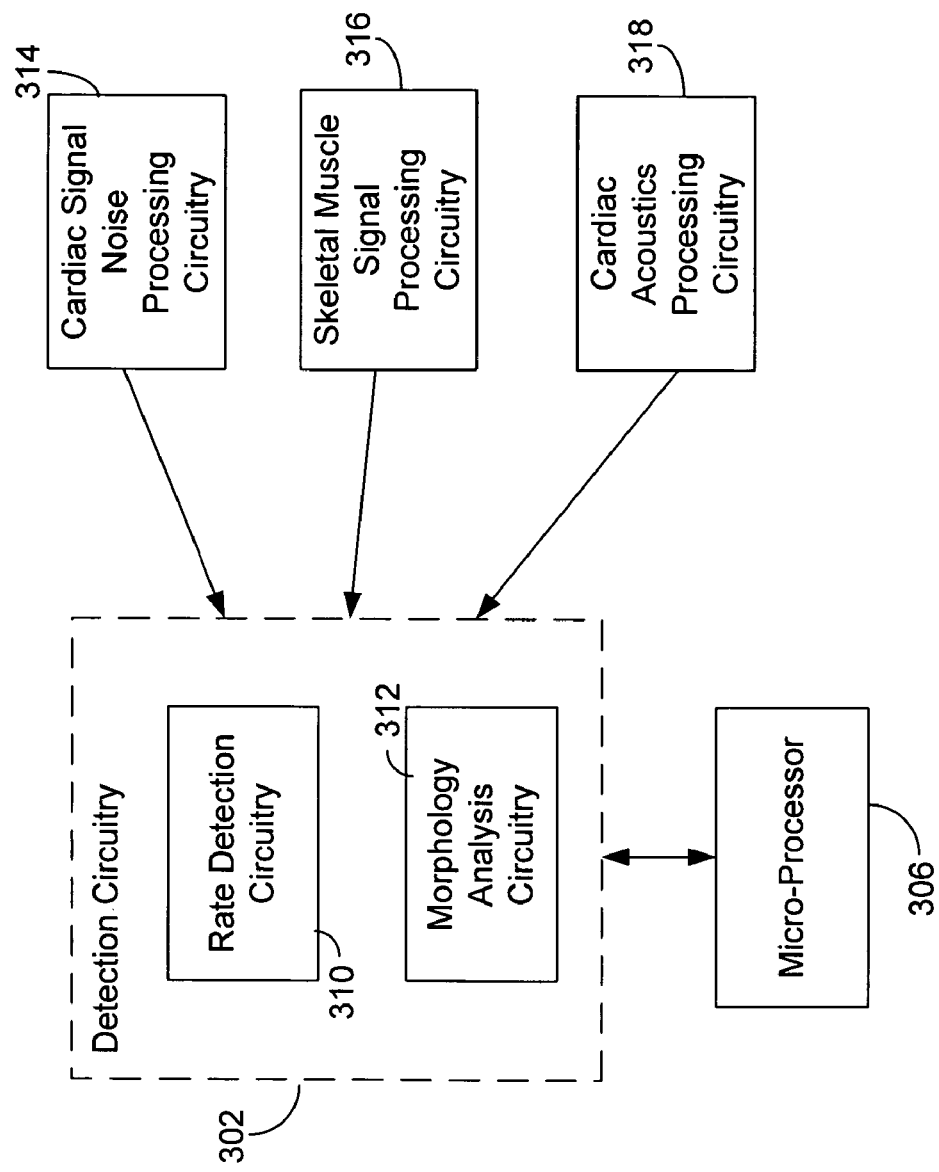
FIG. 1D is a block diagram illustrating various processing and detection components of a transthoracic cardiac sensing and/or stimulation device in accordance with an embodiment of the present invention.

FIG. 1D illustrates a configuration of detection circuitry 302 of an ITCS device that includes one or both of rate detection circuitry 310 and morphological analysis circuitry 312. Detection and verification of arrhythmias may be accomplished using rate-based discrimination algorithms as known in the art implemented by the rate detection circuitry 310. Arrhythmic episodes may also be detected and verified by morphology-based analysis of sensed cardiac signals as is known in the art. Tiered or parallel arrhythmia discrimination algorithms may also be implemented using both rate-based and morphologic-based approaches. Further, a rate and pattern-based arrhythmia detection and discrimination approach may be employed to detect and/or verify arrhythmic episodes, such as the approach disclosed in U.S. Pat. Nos. 6,487,443; 6,259,947; 6,141,581; 5,855,593; and 5,545,186, which are hereby incorporated herein by reference in their respective entireties.

An ITCS device may be implemented to include a subcutaneous electrode system that provides for cardiac sensing and arrhythmia therapy. According to this approach, an ITCS device may be implemented as a chronically implantable system that performs monitoring, diagnostic and/or therapeutic functions. The ITCS device may automatically detect and treat cardiac arrhythmias. In one configuration, the ITCS device includes a pulse generator and one or more electrodes that are implanted subcutaneously in the chest region of the body, such as in the anterior thoracic region of the body. The ITCS device may be used to provide atrial and ventricular therapy for bradycardia and tachycardia arrhythmias. Tachyarrhythmia therapy may include cardioversion, defibrillation and anti-tachycardia pacing (ATP), for example, to treat atrial or ventricular tachycardia or fibrillation. Bradycardia therapy may include temporary post-shock pacing for bradycardia or asystole. Methods and systems for implementing post-shock pacing for bradycardia or asystole are described in commonly owned U.S. patent application entitled "Subcutaneous Cardiac Stimulator Employing Post-Shock Transthoracic Asystole Prevention Pacing, Ser. No. 10/377,274, filed on Feb. 28, 2003, which is incorporated herein by reference in its entirety.

An ITCS device of a type described herein may be used within the structure of an advanced patient management (APM) system. Advanced patient management systems may allow physicians to remotely and automatically monitor cardiac and respiratory functions, as well as other patient conditions. In one example, implantable cardiac rhythm management systems, such as cardiac pacemakers, defibrillators, and resynchronization devices, may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Figure 2A:
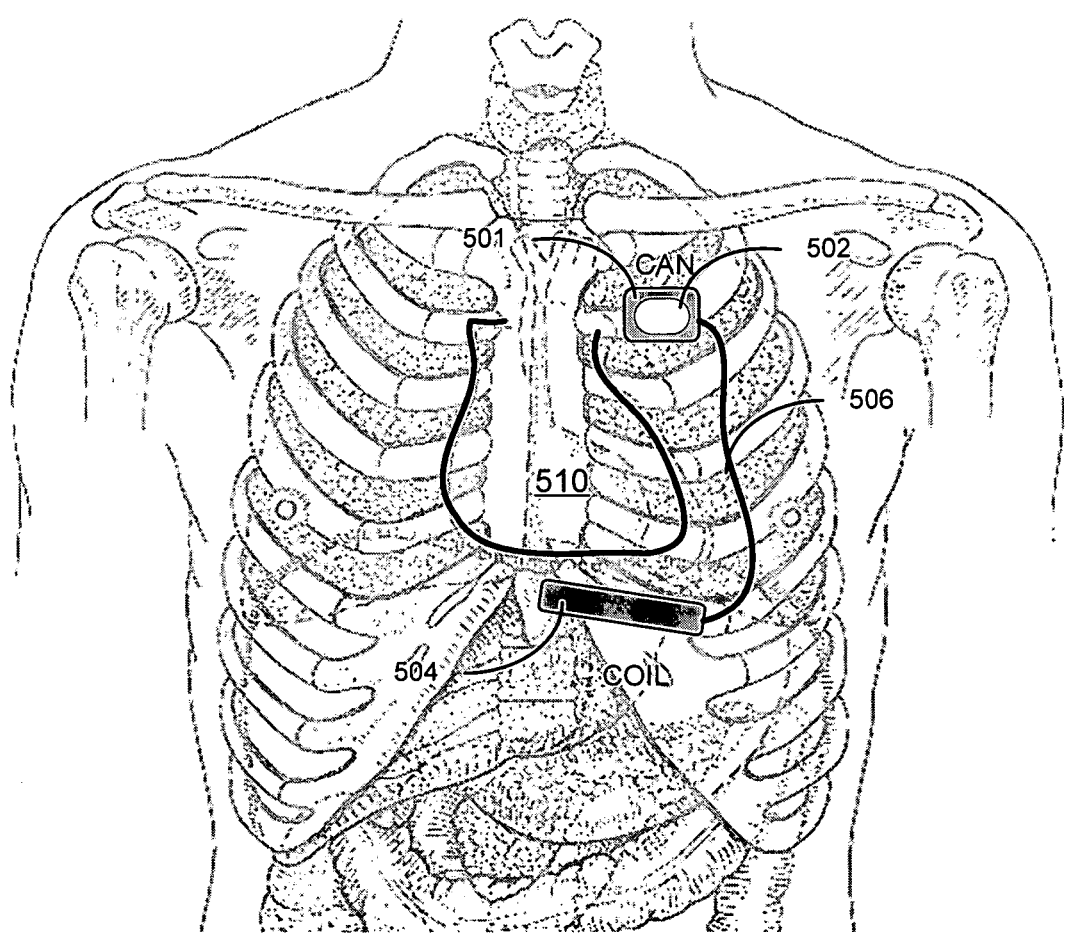
FIGS. 2A–2C are diagrams illustrating various components of a transthoracic cardiac sensing and/or stimulation device located in accordance with embodiments of the invention.

In one configuration, illustrated in FIG. 2A, electrode subsystems of the ITCS system include a first electrode subsystem, comprising a can electrode 502, and a second electrode subsystem 504 that may include at least one coil electrode, for example. The second electrode subsystem 504 may include a number of electrodes used for sensing and/or electrical stimulation. In various configurations, the second electrode subsystem 504 may include a single electrode or a combination of electrodes. The single electrode or combination of electrodes comprising the second electrode subsystem 504 may include coil electrodes, tip electrodes, ring electrodes, multi-element coils, spiral coils, spiral coils mounted on non-conductive backing, and screen patch electrodes, for example. A suitable non-conductive backing material is silicone rubber, for example.

The can electrode 502 is located on the housing 501 that encloses the ITCS device electronics. In one embodiment, the can electrode 502 includes the entirety of the external surface of housing 501. In other embodiments, various portions of the housing 501 may be electrically isolated from the can electrode 502 or from tissue. For example, the active area of the can electrode 502 may include all or a portion of either the anterior or posterior surface of the housing 501 to direct current flow in a manner advantageous for cardiac sensing and/or stimulation.

The housing 501 may resemble that of a conventional implantable ICD, is approximately 20–100 cc in volume, with a thickness of 0.4 to 2 cm and with a surface area on each face of approximately 30 to 100 $cm^2$. As previously discussed, portions of the housing may be electrically isolated from tissue to optimally direct current flow. For example, portions of the housing 501 may be covered with a non-conductive, or otherwise electrically resistive, material to direct current flow. Suitable non-conductive material coatings include those formed from silicone rubber, polyurethane, or parylene, for example.

FIG. 2A illustrates the housing 501 and can electrode 502 placed subcutaneously, superior to the heart 510 in the left pectoral region, which is a location commonly used for conventional pacemaker and defibrillator implants. The second electrode subsystem 504 may include a coil electrode mounted on the distal end of a lead body 506, where the coil is approximately 3–15 French in diameter and 5–12 cm in length. The coil electrode may have a slight preformed curve along its length. The lead may be introduced through the lumen of a subcutaneous sheath, through a common tunneling implant technique, and the second electrode subsystem 504, e.g., comprising a coil electrode, may be placed subcutaneously, deep to any subcutaneous fat and adjacent to the underlying muscle layer.

In this configuration, the second electrode subsystem 504 is located approximately parallel with the inferior aspect of the right ventricle of the heart 510, just inferior to the right ventricular free wall, with one end extending just past the apex of the heart 510. For example, the tip of the electrode subsystem 504 may extend less than about 3 cm and may be about 1–2 cm left lateral to the apex of the heart 510. This electrode arrangement may be used to include a majority of ventricular tissue within a volume defined between the housing 501 and the second electrode subsystem 504. In one configuration, a majority of the ventricular tissue is included within a volume associated with an area bounded by lines drawn between the distal and proximal ends of the second electrode subsystem 504 and the medial and lateral edges of the left pectoral can electrode 502.

In one example arrangement, the volume including a majority of ventricular tissue may be associated with a cross sectional area bounded by lines drawn between the ends of the electrode subsystems 502, 504 or between active elements of the electrode subsystems 502, 504. In one implementation, the lines drawn between active elements of the electrode subsystems 502, 504 may include a medial edge and a lateral edge of the can electrode 502, and a proximal end and a distal end of a coil electrode utilized within the second electrode subsystem 504. Arranging the electrode subsystems so that a majority of ventricular tissue is contained within a volume defined between the active elements of the electrode subsystems 502, 504 provides an efficient position for defibrillation by increasing the voltage gradient in the ventricles of the heart 510 for a given applied voltage between electrode subsystems 502, 504.

Figure 2B:
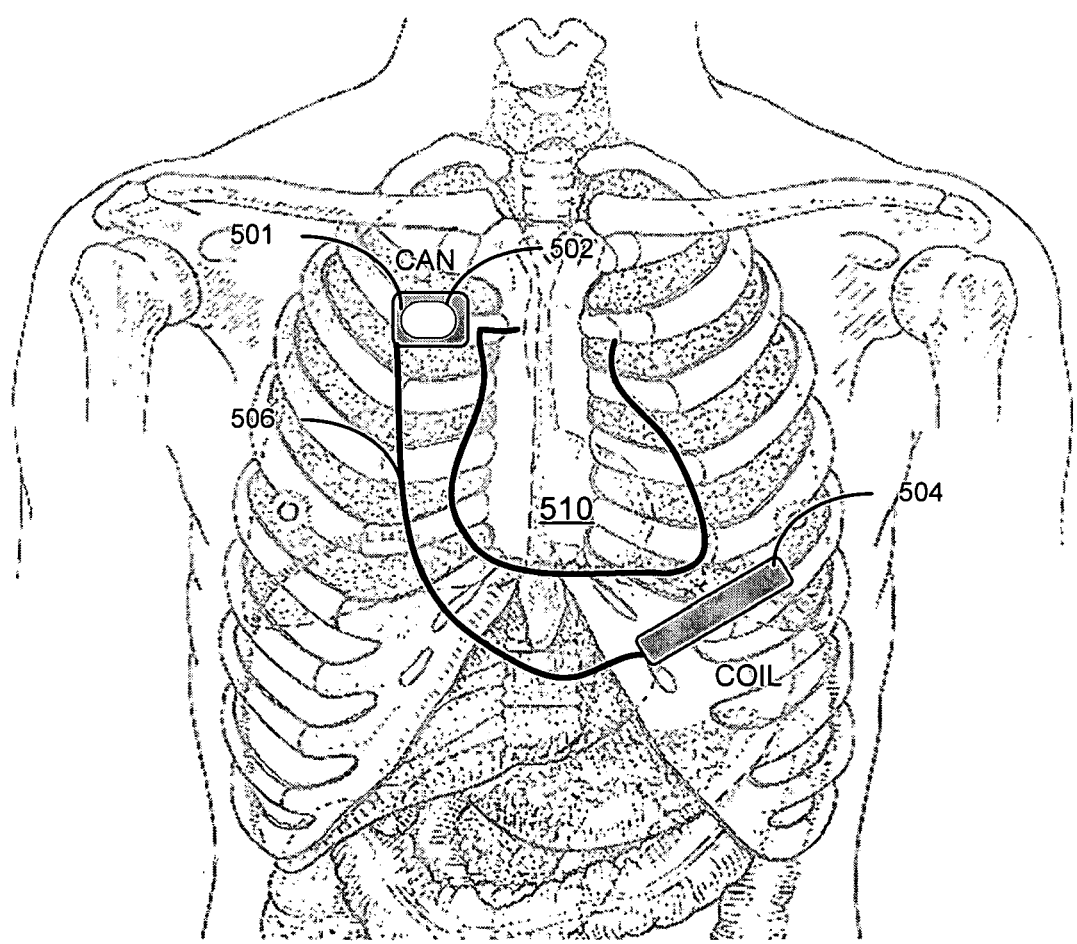

In a similar configuration, and as shown in FIG. 2B, the housing 501 comprising the can electrode 502 is placed in the right pectoral region. The second electrode subsystem 504 is located more laterally, to again include a majority of the ventricular tissue in a volume defined between the can electrode 502 and the second electrode subsystem 504.

Figure 2C:
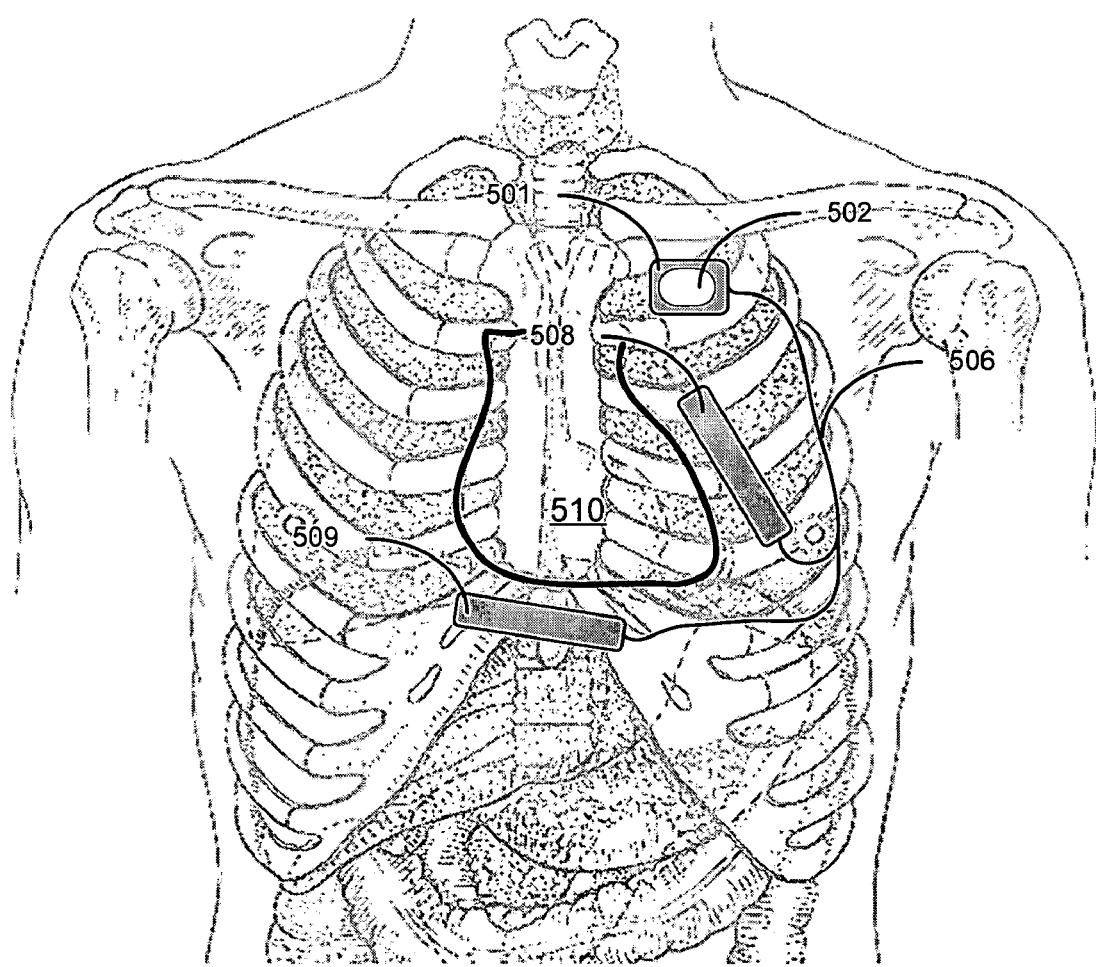

In a further configuration, and as shown in FIG. 2C, the ITCS device housing 501 containing the electronics (i.e., the can) is not used as an electrode. In this case, an electrode system comprising two electrode subsystems 508, 509 coupled to the housing 501 may be implanted subcutaneously in the chest region of the body, such as in the anterior thorax. The first and the second electrode subsystems 508, 509 are placed in opposition with respect to the ventricles of the heart 510, with the majority of the ventricular tissue of the heart 510 included within a volume defined between the electrode subsystems 508, 509. As illustrated in FIG. 2C, the first electrode system 508 is located superior to the heart 510 relative to a superior aspect of the heart 510, e.g., parallel to the left ventricular free wall. The second electrode system 509 is located inferior to the heart 510 and positioned in relation to an inferior aspect of the heart 510, e.g., parallel to the right ventricular free wall.

In this configuration, the first and the second electrode subsystems 508, 509 may include any combination of electrodes, including or excluding the can electrode, used for sensing and/or electrical stimulation. In various configurations, the electrode subsystems 508, 509 may each be a single electrode or a combination of electrodes. The electrode or electrodes comprising the first and second electrode subsystems 508, 509 may include any combination of one or more coil electrodes, tip electrodes, ring electrodes, multi-element coils, spiral coils, spiral coils mounted on non-conductive backing, and screen patch electrodes, for example.

Figure 3A:
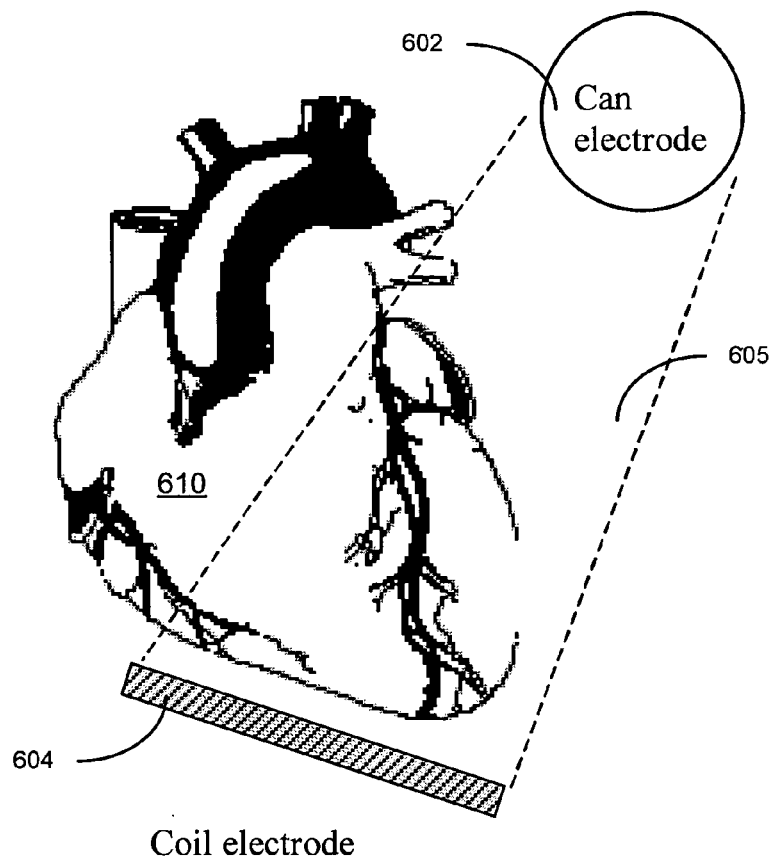
FIGS. 3A–3C are diagrams illustrating electrode subsystem placement relative to a heart in accordance with embodiments of the invention.
Figure 3B:
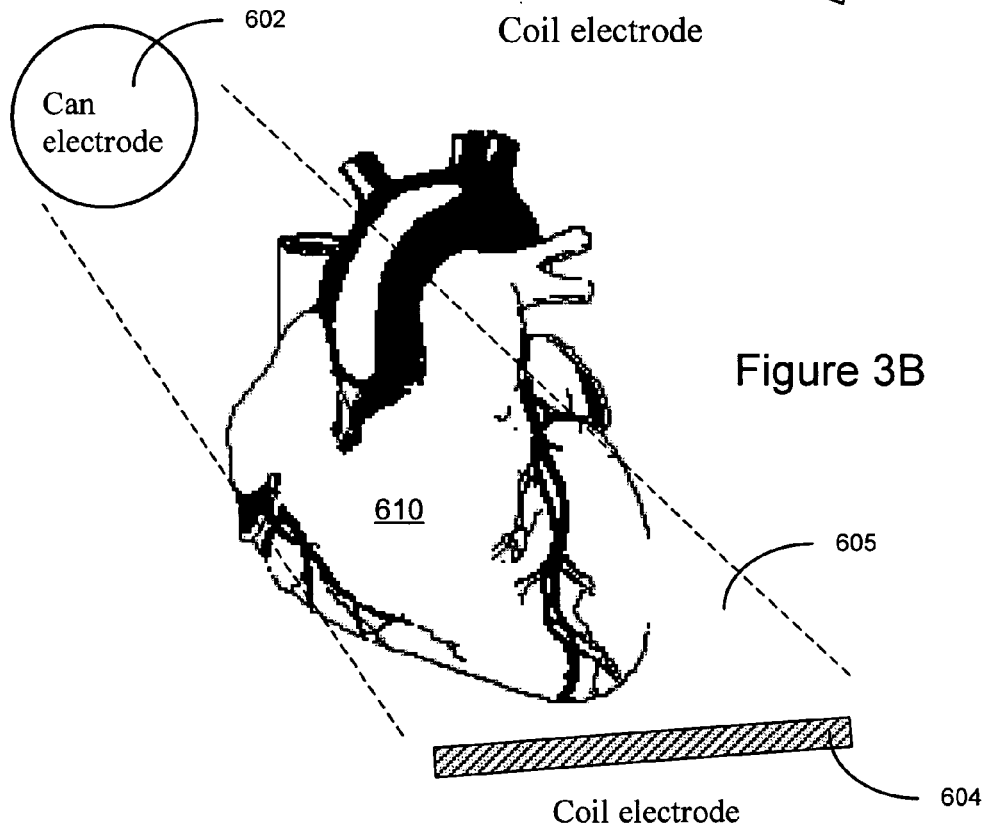
Figure 3C:
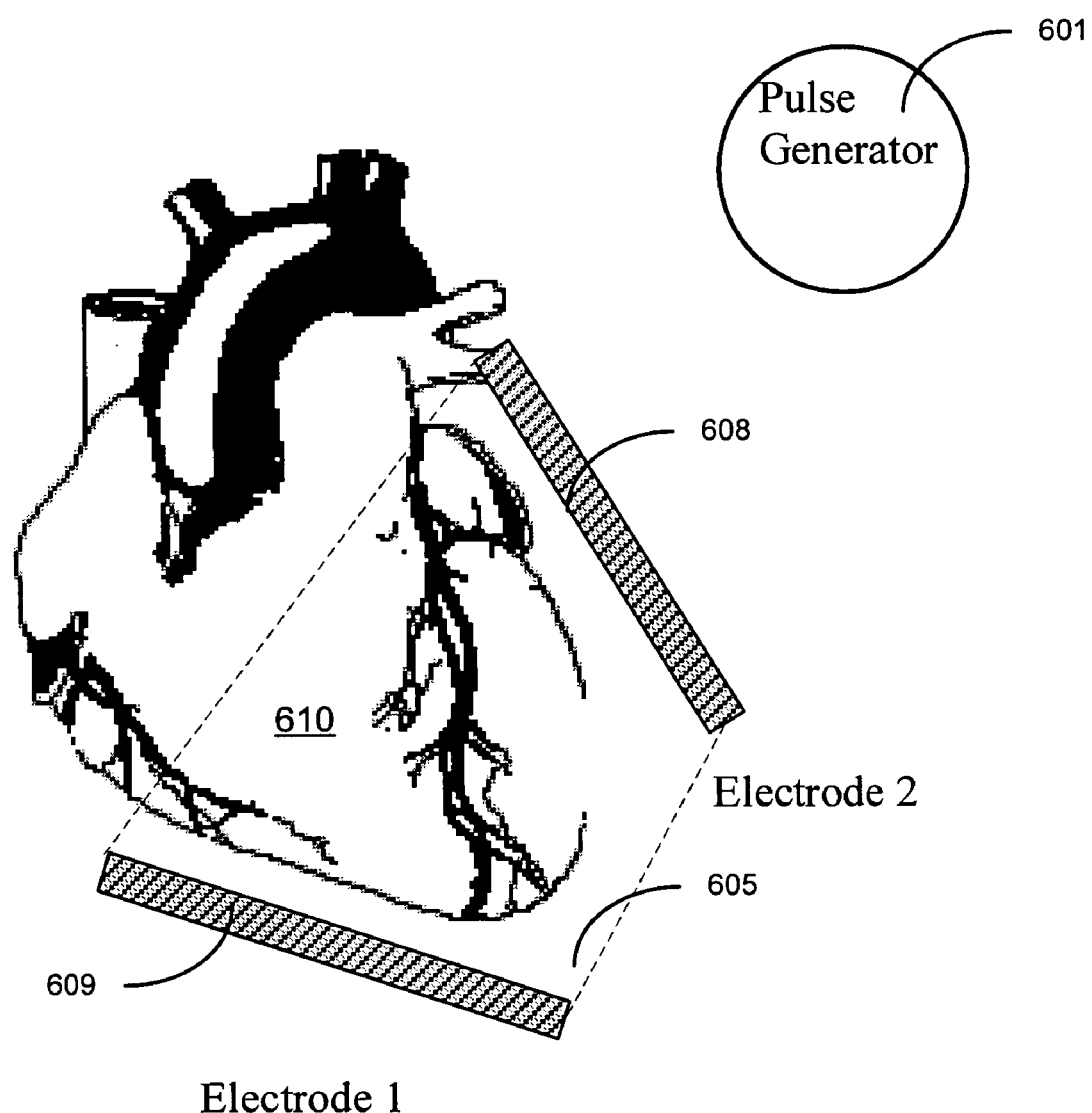

FIGS. 3A–3C provide additional detailed views of subcutaneous electrode subsystem placement considered particularly useful in patient implant stratification in accordance with embodiments of the present invention. FIG. 3A illustrates first and second electrode subsystems configured as a can electrode 602 and a coil electrode 604, respectively. FIG. 3A illustrates the can electrode 602 located superior to the heart 610 in the left pectoral region and the coil electrode 604 located inferior to the heart 610, parallel to the right ventricular free wall of the heart 610.

The can electrode 602 and the coil electrode 604 are located so that the majority of ventricular tissue is included within a volume defined between the can electrode 602 and the coil electrode 604. FIG. 3A illustrates a cross sectional area 605 formed by the lines drawn between active elements of the can electrode 602 and the coil electrode 604. Lines drawn between active areas of the electrodes 602, 604, may be defined by a medial edge and a lateral edge of the can electrode 602, and a proximal end and a distal end of a coil electrode utilized as the second electrode subsystem 604. The coil electrode 604 extends a predetermined distance beyond the apex of the heart 610, e.g. less than about 3 cm.

A similar configuration is illustrated in FIG. 3B. In this embodiment, the can electrode 602 is placed superior to the heart 610 in the right pectoral region. The coil electrode 604 is located inferior to the heart. In one arrangement, the coil electrode is located relative to an inferior aspect of the heart 610, for example, the apex of the heart. The can electrode 602 and the coil electrode 604 are positioned so that the majority of ventricular tissue is included within a volume defined between the can electrode 602 and the coil electrode 604.

FIG. 3B illustrates a cross sectional area 605 formed by the lines drawn between active elements of the can electrode 602 and the coil electrode 604. Lines drawn between active areas of the electrodes 602, 604, may be defined by a medial edge and a lateral edge of the can electrode 602, and a proximal end and a distal end of a coil electrode utilized as the second electrode subsystem 604. The coil electrode 604 extends a predetermined distance beyond the apex of the heart 610, e.g. less than about 3 cm.

FIG. 3C illustrates a configuration wherein the pulse generator housing 601 does not include an electrode. In this implementation two electrode subsystems are positioned about the heart so that a majority of ventricular tissue is included within a volume defined between the electrode subsystems. According to this embodiment, the first and second electrodes are configured as first and second coil electrodes 608, 609. The first coil electrode 608 is located superior to the heart 610 and may be located relative to a superior aspect of the heart, e.g., the left ventricular free wall. The second coil electrode 609 is located inferior to the heart 610. The second electrode 609 may be located in relation to an inferior aspect of the heart 610. In one configuration, the second electrode 609 is positioned parallel to the right ventricular free wall with a tip of the electrode 609 extending less than about 3 cm beyond the apex of the heart 610. As illustrated in FIG. 3C, the volume defined between the electrodes may be defined by the cross sectional area 605 bounded by lines drawn between active areas of the electrodes 608, 609.

As described above, many variations in device and system configuration are possible that are beneficial to the patient. Anatomical variations and other factors affect the capabilities and efficacy of implantable cardiac monitoring and stimulation systems. Embodiments of the present invention are directed to systems and methods for evaluating and verifying that the systems described above or other implantable systems are capable of operating as intended in a particular patient. Embodiments of the present invention are also directed to systems and methods for determining proper placement of components of these implantable systems. Embodiments of the present invention are further directed to systems and methods for determining signal levels useful for individual patient stratification, and signal levels that provide efficacy of subcutaneous defibrillation devices implantable within a given patient.

Using, for example, a subcutaneous defibrillator having components such as those illustrated in FIGS. 2A and 2B, embodiments of the present invention will be described with reference to FIGS. 3D and 4A–4C. It should be understood that use of a subcutaneous defibrillator is by way of example only, and that the present invention may be implemented in or with other systems and/or devices disclosed herein either directly or by reference.

Figure 3D:
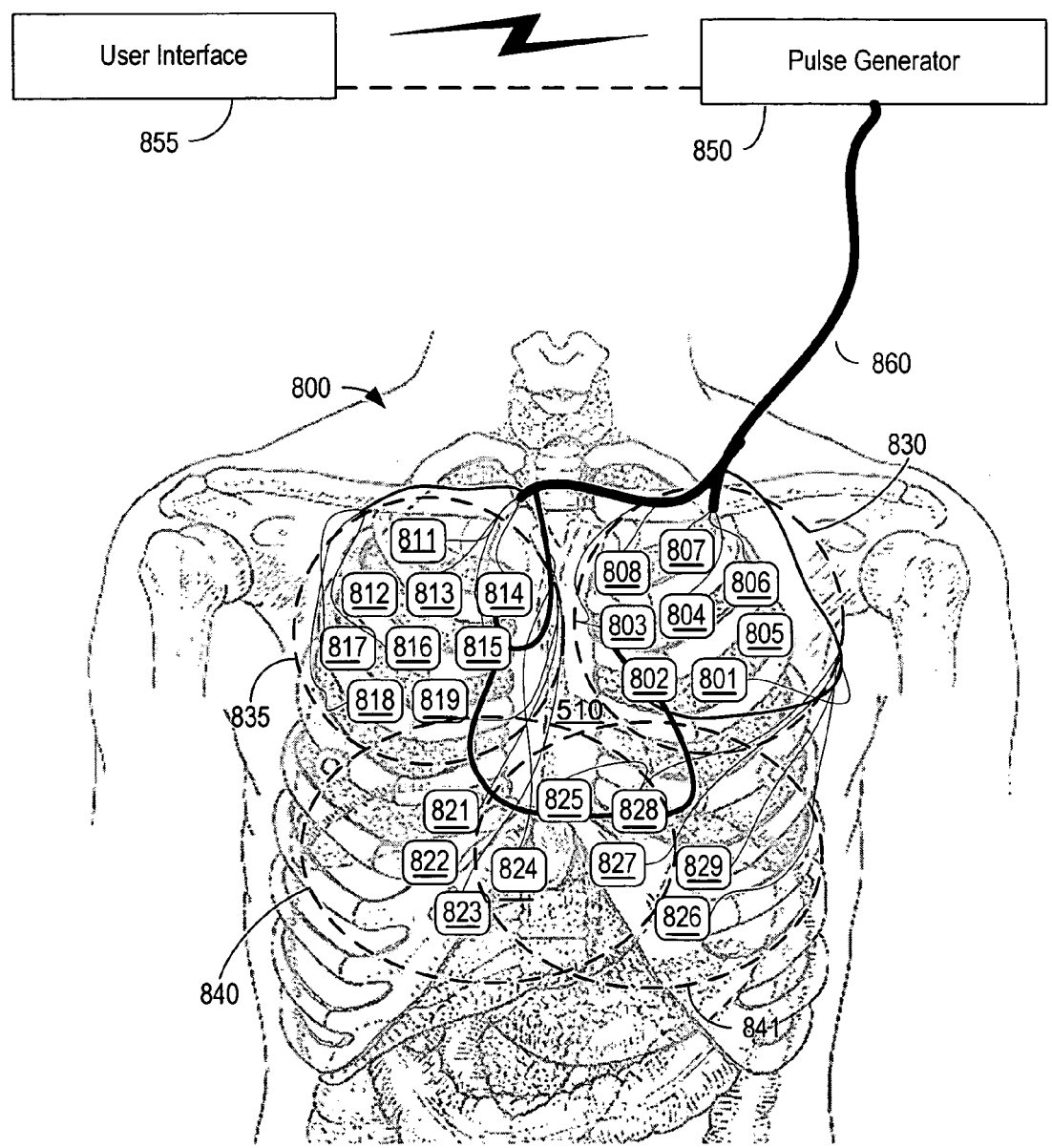
FIG. 3D illustrates electrode placement and an electrode testing system in accordance with an embodiment of the present invention.

Referring now to FIG. 3D, many potential locations 800 for locating various subcutaneous defibrillator components are illustrated. Depending on the particular system intended for the patient, and the anatomical variation of the patient, proper locations should be identified for purposes of improving or optimizing component placement. For example, consider an individual patient identified as a potential candidate for implantation of a system as described with reference to FIGS. 2A and 2B. Referring to FIGS. 2A–2B and FIG. 3D, locations 811 through 819 depict possible right-pectoral locations for placement of the active can 501 of the implantable subcutaneous defibrillator. Locations 801 through 808 depict possible left-pectoral locations for placement of the active can 501 of the implantable subcutaneous defibrillator. Locations 821 through 829 depict possible locations for the coil 504 of the implantable subcutaneous defibrillator.

Defibrillation thresholds typically vary from patient to patient, with some thresholds being beyond the capabilities of some defibrillators. Since surgery is required for implantation of subcutaneous defibrillation devices such as described herein, it is desirable to avoid subjecting patients to an implantation procedure if they are not good candidates for a given system.

The inventors have discovered that, since subcutaneous defibrillation electrodes are generally located away from the heart relative to transvenous defibrillation electrodes, for example, there is a proportionality relationship between surface pacing levels and subcutaneous defibrillation levels that can be advantageously exploited for a number of purposes. This proportionality relationship has been found to be valid when electrodes of a subcutaneous defibrillation device are located relative to the heart within a predefined region of the patient's thorax.

Embodiments of the present invention exploit this relationship for verifying that the implantable systems operate as intended in a particular patient, making that patient a candidate for implantation of the particular defibrillation system. Embodiments of the present invention also use this proportionality relationship for determining proper placement of components of a given implantable defibrillation system. Embodiments of the present invention further use this proportionality relationship for determining stimulus levels useful for individual patient stratification. In other embodiments of the present invention, this proportionality relationship is useful for stratifying patients. Examples of patient stratification include determining that a patient is not a candidate for implantation of a 40-Joule defibrillator, but is a candidate for implantation of an 80-Joule defibrillator, or determining that a smaller implantable device is suitable for a patient, thereby saving that patient from the increased bulk of a larger system. It is understood that these examples are for illustration only, and not limitation.

Due to the relationship between subcutaneous defibrillation levels and surface pacing levels, regions of anatomy may be defined for placement of implantable system components. Still referring to FIG. 3D, a region 830, a region 840, and a region 841 may be defined wherein the relationship between a surface pacing level necessary to capture the heart of a patient is proportional to the subcutaneous defibrillation level necessary to defibrillate the heart during an arrhythmic episode.

Within the region 830, it would be desirable to provide an indication of a particular location associated with the lowest surface pacing level that captures the patient's heart, which would correspond to a desirable subcutaneous implant location for the active can in FIG. 2A. In general, the location of the lowest surface pacing level that effects capture within the region 830 corresponds to the position where the lowest subcutaneous defibrillation threshold level may be realized. Similarly, a region 835 in the right pectoral region may be defined with the regions 840, 841 for a two element subcutaneous defibrillation system, or any of the regions 830, 835, and 840, 841 may be defined for a three or more element subcutaneous defibrillation system.

With sufficient clinical data, the proportionality relationship between surface pacing level and subcutaneous defibrillation level may be sufficiently established for a given subcutaneous defibrillation device to exclude patients from candidacy for a given system based solely on surface pacing/capture determinations. Further, patients may be distinguished as candidates for a defibrillator without subjecting the patient to defibrillation testing. Eliminating defibrillation testing (subjecting a patient to additional arrhythmia episodes and defibrillation shocks) reduces the discomfort and risk associated with defibrillation system implant procedures. However, if defibrillation tests are required, the use of the surface electrodes allows the patient not to be subjected to surgery before he/she is determined to be a candidate for the subcutaneous defibrillation system.

Still referring to FIG. 3D, an embodiment of the present invention is illustrated where a patient stratification and electrode location selection process in accordance with embodiments of the present invention are automated. According to one embodiment, an automated system includes a pulse generator 850 connected by a cable 860 to a number of electrodes 800. The pulse generator 850 may also be connected either directly or wirelessly to a user interface 855. The electrodes 800 are shown to include a grouping of the electrodes 811 through 819 within the region 835, a grouping of the electrodes 801 through 808 within the region 830, and a grouping of the electrodes 821 through 829 within the regions 840 and 841.

The electrodes 800 may be individually placed and relocated, or may be provided in one or more groups attached to a substrate such as an adhesive backed polymeric sheet. The electrodes may be large electrodes, such as having an active surface area of about 32 $cm^2$, or may include one or more smaller electrodes, such as standard surface EKG electrodes, that may be used individually or in combination. For example, an array of standard EKG surface electrodes may be used, and adjacent pairs or combinations of electrodes may be used simultaneously for pacing and/or defibrillation.

The pulse generator 850 may be used to facilitate selection of appropriate subcutaneous implant locations by scanning through select individual or groups of surface electrodes. For example, the pulse generator 850 may select two electrodes, electrode 807 and 825, as potential locations. The pulse generator 850 may then, send a pacing stimulus at a first surface pacing level using the electrodes 807 and electrode 825. The pacing stimulus may be monophasic, biphasic, or multiphasic (e.g., triphasic). The pulse generator 850 may then detect any cardiac response to the first pacing stimulus, such as capture or non-capture. In another embodiment, capture may be detected using another external device, such as a blood sensor (e.g., pulse oximeter), to mitigate noise such as skeletal muscle artifacts. The pulse generator 850 may systematically scan through several groups of electrodes until appropriate subcutaneous implant locations are determined. Systems and methods for capture detection, threshold sensing, and pulse generation are known in the art, and more fully described in the references previously incorporated by reference.

Figure 4A:
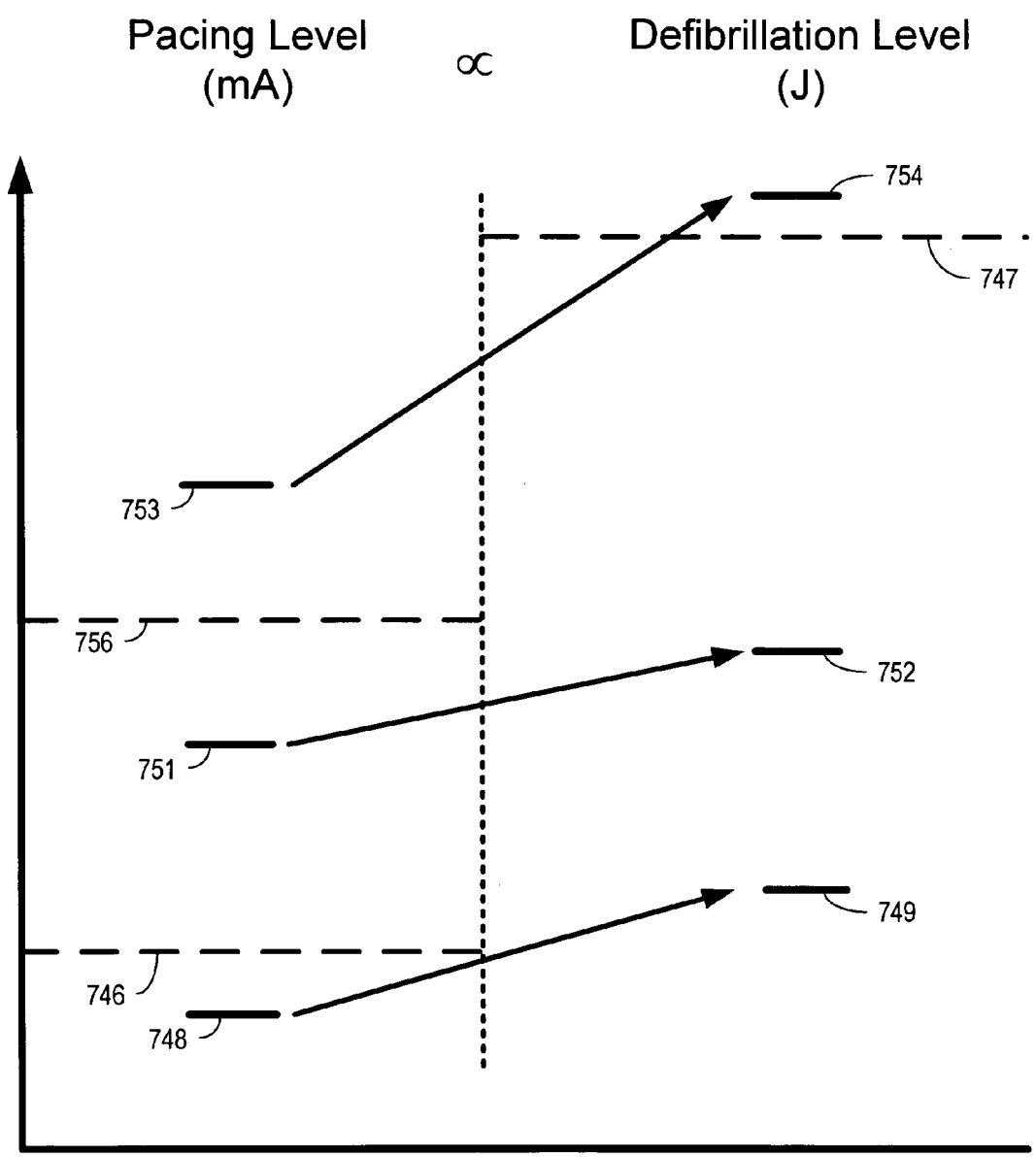
FIG. 4A is a graph of proportionality relationships between surface pacing and subcutaneous defibrillation stimulus levels.

Referring to FIG. 4A, a graph illustrates a proportionality relationship between surface pacing level and subcutaneous defibrillation level. Illustrated in FIG. 4A is a surface pacing level 748 corresponding, through a proportionality transfer function, to a defibrillation level 749. Likewise, a surface pacing level 751 corresponds, through the proportionality transfer function, to a subcutaneous defibrillation level 752 and a surface pacing level 753 corresponds, through the proportionality transfer function, to a subcutaneous defibrillation level 754.

A surface pacing acceptance level 746 is shown, below which a subcutaneous defibrillation device may be established as acceptable for implantation in a patient if the patient's capture threshold falls at or below the acceptance level 746. An upper limit 747 may be established for a given subcutaneous defibrillation device, above which the subcutaneous defibrillation device has insufficient energy to provide defibrillation to a patient, either to defibrillate the heart or to ensure a sufficient lifetime of the subcutaneous defibrillation device.

If a patient's capture threshold associated with surface pacing exceeds the predetermined upper limit 756, the patient would be contra-indicated for implantation of a given implantable subcutaneous defibrillation device. A patient having the surface pacing level 751 may be above the acceptance level 746 for automatic acceptance, and below the predetermined upper limit 756 for patient contra-indication. Patients in this category may require further testing, such as using defibrillation testing, as will be further described below.

Figure 4B:
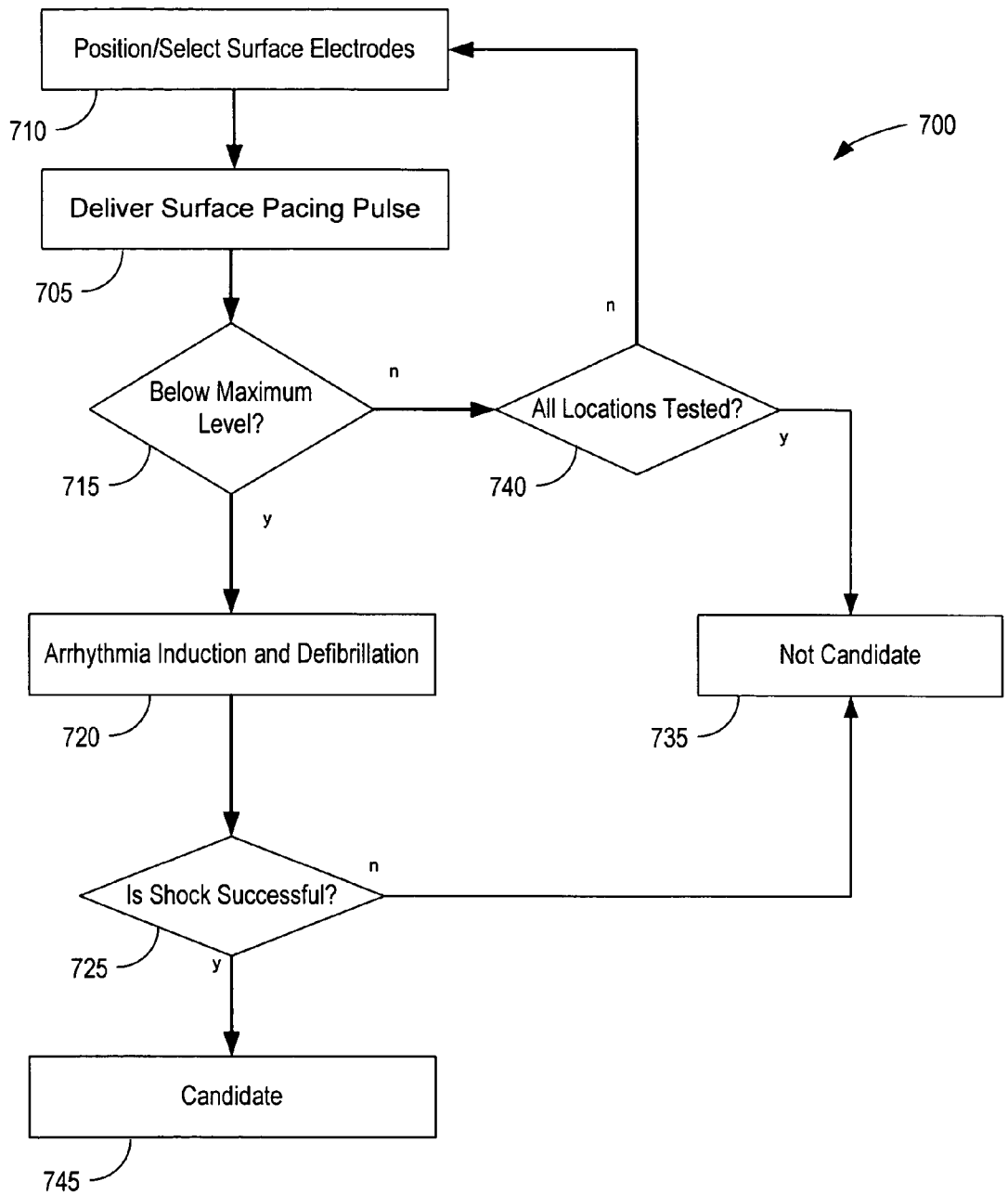
FIG. 4B is a flow-chart of a method for performing patient stratification in accordance with the present invention.

Referring now to FIG. 4B, a patient selection and/or stratification method 700 is illustrated. The patient selection and/or stratification method 700 begins with surface electrode placement 710 or selection (e.g., within an array of electrodes). The electrodes located during surface electrode placement 710 are then used for pacing by delivering a surface pacing pulse 705, and capture/non-capture is sensed to determine if capture may be achieved below an upper surface pacing level 715, such as a predetermined upper level. The predetermined upper level may be, for example, the level above which the associated defibrillation energy level is beyond the capability of the defibrillator.

A determination 740 is made until acceptable electrode positions are located that provide pacing levels for capture below the upper surface pacing level 715. If no electrode positions can be found below the upper surface pacing level 715, then it is determined 735 that the patient is not a candidate for the subcutaneous defibrillation device. If acceptable electrode positions are located that provide pacing levels below the upper surface pacing level 715, then the patient may be subjected to a defibrillation test 720 to verify that the defibrillation device properly terminates the induced tachyarrhythmia at those electrode positions. The defibrillation test 720 may use a surface defibrillation shock that may be monophasic, biphasic, or multiphasic (e.g., triphasic), and have a desired tilt.

If the determination at block 725 shows that the defibrillation test 720 was not successful, then it is determined 735 that the patient is not a candidate for the subcutaneous defibrillation device, and an intervention may be performed if necessary, such as performing a higher amplitude defibrillation shock, altering the polarity and/or otherwise altering the defibrillation waveform. If the determination at block 725 shows that the defibrillation test 720 was successful, then the patient is determined to be a candidate 745 for the subcutaneous defibrillation device. The patient selection and/or stratification method 700 is illustrative of a process that may be implemented using an automated (fully automatic or semi-automatic) electrode scanning system, or may be performed by a clinician using repositionable surface electrodes.

It is also contemplated by the inventors that an automated stratification system may be built into an implantable ITCS device, to further stratify patients during the continued lifetime of the implant. For example, patient stratification may be an automated process post-implant, or performed routinely at patient follow-ups. This periodic stratification may identify patients who may need to have a device upgrade because of, for example, increased body weight, progression of heart disease, or other pathological or physiological conditions. As described earlier, results of such routine stratifications may be communicated via an advanced patient management system. Implantable systems that detect capture and that may be useful with embodiments of the present invention that perform routine patient stratification are further described in U.S. Pat. Nos. 5,683,431; and 5,331,966, hereby incorporated herein by reference.

Figure 4C:
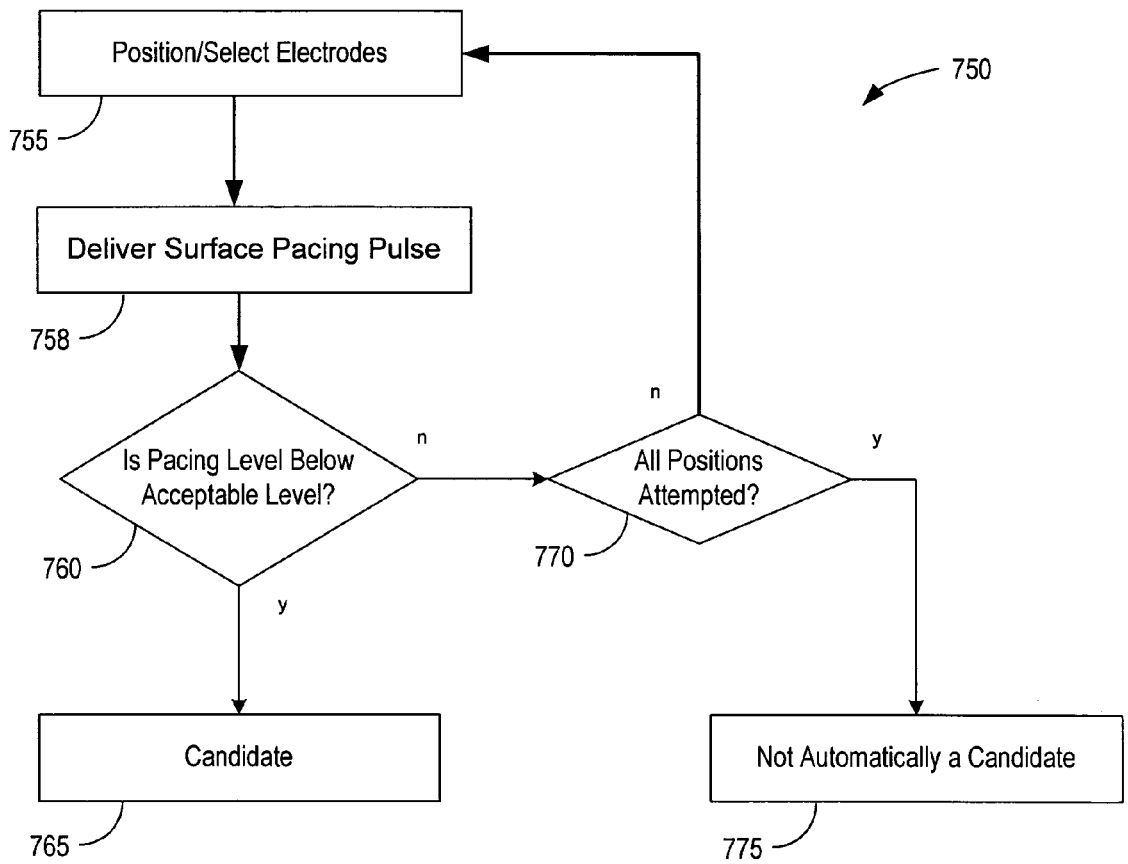
FIG. 4C is a flow-chart of another method for performing patient stratification in accordance with an embodiment of the present invention.

As described earlier, sufficient clinical data may eliminate the need for defibrillation testing altogether. The method illustrated in FIG. 4C shows a simplified method 750 where the proportionality between the surface pacing levels and implant levels are known. The patient selection and/or stratification method 750 begins with a surface electrode placement 755 (or selection among a group or array of electrodes, as described earlier). The electrodes at the surface electrode placement 755 are then used for pacing by delivering a surface pacing pulse 758, and capture/non-capture is sensed to determine if capture may be achieved below a surface pacing level 760, such as a predetermined acceptance level. The predetermined acceptance level may be, for example, the level below which the associated defibrillation energy level of the subcutaneous defibrillation device is established as acceptable and the proportionality relationship between the surface parameters and the implant parameters is valid.

A determination at block 770 is made until acceptable surface electrode positions are located that provide pacing levels that effect capture below the surface pacing level 760. If no electrode positions can be found that provide pacing levels that effect capture below the surface pacing level 760, then the patient is determined to not be an automatic candidate 775 for the subcutaneous defibrillation device. The patient may then undergo the patient selection and/or stratification method 700 of FIG. 4B, or test for an alternate implantable subcutaneous defibrillation system. If acceptable surface electrode positions are located that provide pacing levels that effect capture below the surface pacing level 760, then the patient is a candidate 765 for the subcutaneous defibrillation device.

In another embodiment of the present invention, the electrodes may be affixed to an electrode support assembly, and have a predefined positional relationship relative to one another. A patient screening method using this type of electrode arrangement may involve the steps of providing at least two surface electrodes connected together and having a fixed spatial relationship. The electrodes may then be located on a thorax of a patient, such as having a first electrode near the apex of the patient's heart, and having a second electrode at a left pectoral region of the patient's thorax.

A surface pacing threshold may be determined for effecting cardiac capture using the surface electrodes. The patient may be selected or rejected as a candidate for implantation of a subcutaneous defibrillation system based on the surface pacing threshold. If the current positioning is not acceptable, the electrode support assembly may be rotated about the first electrode, for example, by maintaining the first electrode at the heart's apex, but rotating the second electrode to another location. For example, the second electrode may be rotated from the left pectoral region of the patient's thorax to a right pectoral location of the patient's thorax in search of a more optimum pacing and/or defibrillation threshold. The first electrode may be repositioned as well, if desired.

The electrode support assembly maintains the predefined positional relationship of the electrodes as they are positioned and rotated on the patient's thorax. The electrode support assembly may be constructed to be substantially rigid or somewhat flexible. The electrode assembly may have an elastic, spring, or mechanical memory that retains a desired configuration after being shaped or manipulated by a clinician. For example, the electrode support assembly can incorporate a gooseneck or braid system that can be distorted under manual force to take on a desired shape. In this manner, the electrode support assembly can be shape-fit to accommodate the unique anatomical configuration of a given patient, and generally retains a customized shape during the clinical procedure. Shaping of the electrode support assembly according to this configuration can occur prior to, and during, the clinical procedure, if desired.

Figure 5A:
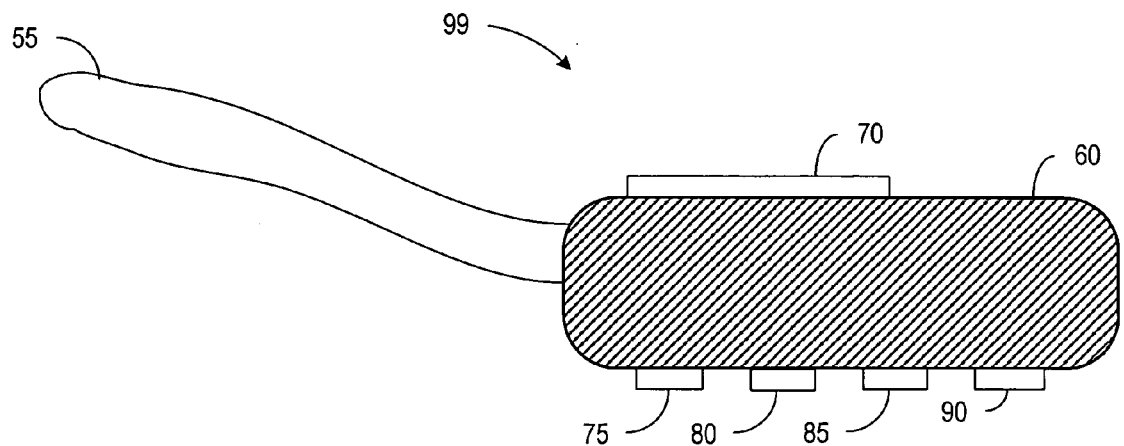
FIGS. 5A and 5B are side and bottom views respectively of a hand-held device in accordance with an embodiment of the present invention.
Figure 5B:
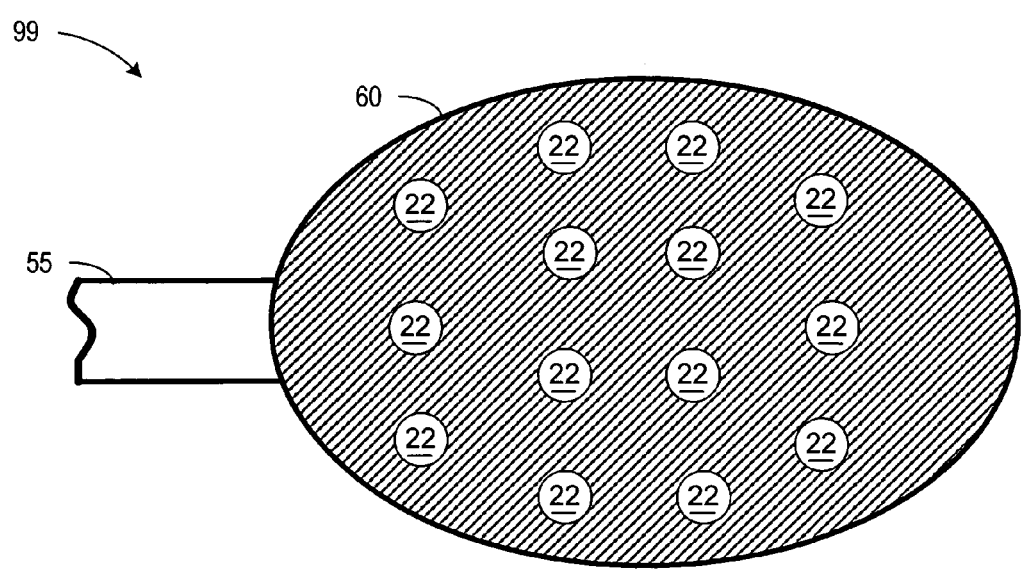

Referring now to FIGS. 5A and 5B, there is illustrated a device 99 that may be used to determine suitable electrode locations in accordance with an embodiment of the present invention. In the particular embodiment shown in FIGS. 5A and 5B, the device 99 is configured as a hand-held device. The device 99 may be configured for stand-alone operation or cooperative use with another processing device (e.g., a display, recording, and/or pulse generator device). A suitable device useful for pacing and defibrillation and modifiable in accordance with embodiments of the present invention is a Philips HeartStart device available from Philips Medical Systems, 3000 Minuteman Road, Andover, Mass. 01810-1099.

FIG. 5A illustrates a side view of the device 99. The device 99 may include a handle 55, a body 60, a user interface 70, and one or more electrodes 75, 80, 85, and 90. The handle 55 may be grasped by a clinician, and the body 60 may be placed over the thorax of a patient. The device 99 may then perform one or more of the methodologies described above to stratify the patient for purposes of implanting a subcutaneous defibrillation device and/or to assist the clinician in determining suitable or optimal subcutaneous electrode implant locations.

Referring to FIG. 5B, a bottom view of the body 60 is illustrated. The body 60 of the device 99 is shown to include a number of electrode locations 22. The electrode locations 22 may be receptacles for connecting electrodes onto the body 60, or may be an array of attached electrodes, such as the electrodes 75, 80, 85, and 90 illustrated in FIG. 5A. The number and positions of electrode locations 22 are shown for illustrative purposes only, and the number, size, and positions of the electrodes or electrode receptacles may vary from those shown in FIGS. 5A and 5B. Moreover, the electrode locations 22 may be stationary, or may be movable to provide the clinician enhanced selectivity with regard to the positions of the electrode locations 22.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A patient screening method, comprising:
    delivering a pacing stimulus to a heart of a patient using one or more surface electrodes, the pacing stimulus delivered at a surface pacing level; and
    determining that the patient is not a candidate for implantation of a subcutaneous defibrillation system if the surface pacing level needed to capture the patient's heart is beyond a predetermined level.

2. The method of claim 1, wherein the surface pacing level corresponds to a subcutaneous defibrillation energy level.

3. The method of claim 1, wherein the patient candidacy determination is based at least in part on a pre-established proportionality relationship between the surface pacing level and a subcutaneous defibrillation level.

4. The method of claim 1, wherein delivering the pacing stimulus comprises positioning the one or more surface electrodes within one or more pre-determined thoracic regions relative to the patient's heart.

5. The method of claim 4, wherein the one or more predetermined thoracic regions define regions where a proportionality relationship between the surface pacing level and a subcutaneous defibrillation energy level is operative.

6. The method of claim 1, wherein the predetermined level corresponds to a level of subcutaneous defibrillation energy above which the subcutaneous defibrillation system is not suited to deliver.

7. The method of claim 1, further comprising determining that the patient is a candidate for implantation of the subcutaneous defibrillation system if the surface pacing level needed to capture the patient's heart is within an acceptance level.

8. The method of claim 1, further comprising stratifying the patient for implantation of the subcutaneous defibrillation system using surface defibrillation tests without subjecting the patient to surgery.

9. The method of claim 8, further comprising defibrillation testing the patient using a cardiac defibrillation stimulus delivered at a surface defibrillation level if the surface pacing level needed to capture the patient's heart is beyond the acceptance level and does not exceed the predetermined limit.

10. The method of claim 9, wherein the subcutaneous defibrillation system is configured to deliver a defibrillation therapy at a subcutaneous defibrillation energy level equal to or greater than the surface defibrillation level.

11. A patient screening method, comprising:
    locating at least two surface electrodes on a thorax of a patient;
    determining a surface pacing threshold for effecting cardiac capture using the at least two surface electrodes; and
    determining if the patient is a candidate for implantation of a subcutaneous defibrillation system based on the surface pacing threshold.

12. The method of claim 11, further comprising;
    relocating at least one of the plurality of surface electrodes on the thorax of the patient;
    after relocating, detecting a second surface pacing threshold; and
    selecting a particular surface electrode location using the first and second surface pacing thresholds.

13. The method of claim 12, wherein selecting the particular surface electrode location comprises selecting a location corresponding to a location suitable for implantation of a subcutaneous cardiac stimulation electrode.

14. The method of claim 12, further comprising implanting the subcutaneous cardiac stimulation electrode at the selected location.

15. The method of claim 11, wherein locating the at least two surface electrodes comprises locating an array of surface electrode elements on the patient's thorax, and selecting the particular surface electrode location comprises scanning the array of surface electrode elements to determine their associated surface pacing thresholds.

16. The method of claim 15, wherein the particular surface electrode location is associated with a surface electrode element of the array that has a lowest associated surface pacing threshold.

17. The method of claim 11, wherein locating the at least two surface electrodes on the thorax of the patient comprises:
locating a first surface electrode of the at least two surface electrodes in relation to a superior aspect of the patient's heart; and
locating a second surface electrode of the at least two surface electrodes in relation to an inferior aspect of the patient's heart.

18. The method of claim 11, wherein locating the at least two surface electrodes on the thorax of the patient comprises locating at least one surface electrode substantially parallel to a ventricular free wall of the patient's heart.

19. The method of claim 11, wherein locating the at least two surface electrodes on the thorax of the patient comprises locating at least one surface electrode substantially parallel to a ventricular free wall of the patient's heart and extending a predetermined distance beyond the apex of the patient's heart.

20. The method of claim 11, further comprising inducing an arrhythmia in the patient using the surface electrodes.

21. The method of claim 20, further comprising delivering defibrillation energy to the patient in response to the induced arrhythmia.

22. The method of claim 20, further comprising stratifying the patient for implantation of one of a plurality of subcutaneous defibrillation systems based at least in part on a defibrillation level that terminates the arrhythmia.

23. A system, comprising:
a pulse generator configured to deliver a pacing stimulus at a pacing level;
detection circuitry;
a plurality of surface electrodes coupled to the pulse generator and to the detection circuitry, the plurality of surface electrodes configured for positioning on a thorax of a patient relative to the patient's heart;
a user interface; and
a controller coupled to the pulse generator, detection circuitry, and user interface, respectively, the controller determining suitability of the patient to receive a subcutaneous defibrillation device based at least in part on detection of capture or non-capture resulting from delivery of the pacing stimulus at the pacing level.

24. The system of claim 23, further comprising a housing, the plurality of surface electrodes electrically coupled to the pulse generator and detection circuitry through the housing.

25. The system of claim 23, further comprising a housing, the plurality of surface electrodes supported by the housing.

26. The system of claim 23, further comprising a housing, the pulse generator and detection circuitry provided in the housing, and the plurality of surface electrodes coupled to the housing.

27. The system of claim 23, further comprising a housing, the pulse generator, detection circuitry, and controller provided in the housing, respectively, and the plurality of surface electrodes coupled to the housing.

28. The system of claim 23, further comprising a housing, the pulse generator, detection- circuitry, controller, and user interface support by the housing, respectively, and the plurality of surface electrodes coupled to the housing.

29. The system of claim 28, wherein the housing comprises a handle and is configured for hand-held portability.

30. The system of claim 23, wherein the controller is configured to operate cooperatively with the user interface to provide a user with an indication of the suitability of the patient to receive the subcutaneous defibrillation device.

31. The system of claim 23, wherein the user interface comprises a display.

32. The system of claim 23, wherein the controller determines patient suitability based at least in part on a pre-established proportionality relationship between the pacing level of the pacing stimulus and a subcutaneous defibrillation level.

33. The system of claim 23, wherein the controller determines that the patient is not suitable to receive the subcutaneous defibrillation device if the pacing level of the pacing stimulus needed to capture the patient's heart is beyond a predetermined level.

34. The system of claim 33, wherein the predetermined level corresponds to a level of subcutaneous defibrillation energy above which the subcutaneous defibrillation device is not suited to deliver.

35. The system of claim 33, wherein the controller determines that the patient is suitable to receive the subcutaneous defibrillation device if the pacing level of the pacing stimulus needed to capture the patient's heart is within an acceptance level.

36. The system of claim 33, wherein the controller stratifies the patient for receiving the subcutaneous defibrillation device if the pacing level of the pacing stimulus needed to capture the patient's heart is beyond an acceptance level and within a predetermined level.

37. A system, comprising:
detection circuitry;
energy delivery circuitry;
a plurality of surface electrodes coupled to the detection and energy delivery circuitry, the plurality of surface electrodes configured for positioning on a patient's thorax relative to the patient's heart;
means, coupled to the detection and energy delivery circuitry, for determining capture or non-capture in response to delivery of a surface pacing stimulus; and
means, coupled to the capture determining means, for determining if the patient is a candidate for implantation of a subcutaneous defibrillation device based at least in part on the capture or non-capture determination.

38. The system of claim 37, wherein the patient candidacy determining means uses a pre-established proportionality relationship between a level of the surface pacing stimulus and a subcutaneous defibrillation level.

39. The system of claim 37, further comprising means for displaying an indication of whether or not the patient is a candidate for implantation of the subcutaneous defibrillation device.

40. The system of claim 37, further comprising means, coupled to the energy delivery circuitry, for inducing an arrhythmia.

41. The system of claim 40, further comprising means for delivering defibrillation energy to the patient in response to inducing the arrhythmia.

42. The system of claim 40, further comprising stratifying the patient for implantation of one of a plurality of subcutaneous defibrillation systems based at least in part on a defibrillation level that terminates the arrhythmia.

43. The system of claim 40, further comprising means for stratifying the patient for implantation of one of a plurality of subcutaneous defibrillation devices.

44. A patient screening method, comprising:
providing at least a pair of surface electrodes situated on a support structure, the pair of surface electrodes comprising a first and second surface electrodes having a fixed spatial relationship relative to one another;
locating the first surface electrode at a first location on a thorax of a patient;
moving the support structure to locate the second surface electrode at a second location on the patient's thorax;
determining a surface pacing threshold for effecting cardiac capture using the first and second surface electrodes; and
determining if the patient is a candidate for implantation of a subcutaneous defibrillation system based on the surface pacing threshold.

45. The method of claim 44, wherein:
the first surface electrode is located relative to an apex of the patient's heart; and
moving the support structure comprises rotating the support structure relative to the first surface electrode location to position the second surface electrode at the second location on the patient's thorax.

46. The method of claim 44, wherein the first surface electrode is located relative to an apex of the patient's heart and the second surface electrode is located in relation to a superior aspect of the patient's heart.

47. The method of claim 46, further comprising rotating the second surface electrode relative to the first surface electrode location while maintaining the fixed spatial relationship.

48. The method of claim 44, wherein the first surface electrode is located in relation to an inferior aspect of the patient's heart and the second surface electrode is located in relation to a superior aspect of the patient's heart.

49. The method of claim 44, further comprising inducing an arrhythmia in the patient using the first and second surface electrodes.

50. The method of claim 49, further comprising delivering defibrillation energy to the patient in response to the induced arrhythmia.

51. The method of claim 49, further comprising stratifying the patient for implantation of one of a plurality of subcutaneous defibrillation systems based at least in part on a defibrillation level that terminates the arrhythmia.

52. The method of claim 44, further comprising relocating the first surface electrode and the second surface electrode to respective new locations on the thorax of the patient.

53. The method of claim 52, wherein the respective new locations are associated with a lowest associated surface pacing threshold.

54. A patient stratification system, comprising:
an electrode support assembly;
a plurality of surface electrodes supported by the electrode support assembly and having a fixed spatial relationship relative to one another, the plurality of surface electrodes configured for positioning on a thorax of a patient relative to the patient's heart;
a pulse generator coupled to the plurality of surface electrodes and configured to deliver a pacing stimulus at a pacing level and a defibrillation stimulus at a defibrillation level;
detection circuitry coupled to the plurality of surface electrodes; and
a controller coupled to the pulse generator and detection circuitry, the controller determining suitability of the patient to receive a subcutaneous defibrillation device based at least in part on detection of capture or non-capture resulting from delivery of the pacing stimulus at the pacing level.

55. The system of claim 54, wherein the controller determines patient suitability based at least in part on a pre-established proportionality relationship between the pacing level of the pacing stimulus and a subcutaneous defibrillation level.

56. The system of claim 54, wherein the controller stratifies the patient for receiving the subcutaneous defibrillation device if the pacing level of the pacing stimulus needed to capture the patient's heart is beyond an acceptance level and within a predetermined level.

57. The system of claim 54, wherein the controller stratifies the patient for receiving the subcutaneous defibrillation device based at least in part on inducing an arrhythmia in the patient and determining the defibrillation level that terminates the arrhythmia.

* * * * *